(12) United States Patent
Klippel-Giese et al.

(10) Patent No.: US 7,713,943 B2
(45) Date of Patent: May 11, 2010

(54) FURTHER USE OF PROTEIN KINASE N BETA

(75) Inventors: Anke Klippel-Giese, Berlin (DE); Jörg Kaufmann, Berlin (DE)

(73) Assignee: Silence Therapeutics Aktiengesellschaft (AG), Berlin (DE)

( * ) Notice: Subject to any disclaimer, the term of this patent is extended or adjusted under 35 U.S.C. 154(b) by 661 days.

(21) Appl. No.: 10/640,274

(22) Filed: Aug. 14, 2003

(65) Prior Publication Data

US 2004/0106569 A1 Jun. 3, 2004

Related U.S. Application Data

(60) Provisional application No. 60/409,570, filed on Sep. 11, 2002.

(30) Foreign Application Priority Data

Aug. 14, 2002 (EP) .................................. 02018572

(51) Int. Cl.
*A61K 31/70* (2006.01)
*C07H 21/04* (2006.01)

(52) U.S. Cl. .......................... 514/44; 536/24.5; 530/350

(58) Field of Classification Search ........................ None
See application file for complete search history.

(56) References Cited

U.S. PATENT DOCUMENTS

| 5,504,103 | A | * | 4/1996 | Bonjouklian et al. | ......... | 514/453 |
| 6,133,032 | A | * | 10/2000 | Monia et al. | ................. | 435/375 |
| 6,605,713 | B1 | | 8/2003 | Furste et al. | | |
| 7,056,704 | B2 | * | 6/2006 | Tuschl et al. | ............... | 435/91.1 |
| 2003/0135033 | A1 | * | 7/2003 | Klippel-Giese et al. | .... | 536/23.1 |
| 2008/0319180 | A1 | | 12/2008 | Khvorova et al. | | |

FOREIGN PATENT DOCUMENTS

| AU | 778474 | | 12/2004 |
| EP | 1 064 944 A1 | * | 1/2001 |
| EP | 1064944 A1 | * | 1/2001 |
| WO | WO 91/19813 | | 12/1991 |
| WO | WO 98/08856 | | 3/1998 |
| WO | WO 00/44895 | | 8/2000 |
| WO | WO 00/73469 | | 12/2000 |
| WO | WO 01/75164 | | 10/2001 |
| WO | WO 2008/009477 | | 1/2008 |

OTHER PUBLICATIONS

Jain, "Barriers to drug delivery in solid tumors", Sci Am. 171(1): 58-65, 1994.*
Gura, "Systems for identifying new drugs are often faulty", Science 278 (5340), 1041-1042, 1997.*
MSNBC News Services, "Mixed results on new cancer drug", Nov. 2000, 1-4.*
Crystal, R.G., Science, vol. 270, Oct. 1995, pp. 404-410.*
Izquierdo, M. Cancer Gene Therapy, 12: 217-227, 2005.*
Shankar, P. et al. JAMA, 293(11): 1367-73, 2005.*
Heidenreich, O., Current Pharmaceutical Biotechnology, 5: 349-354, 2004.*
Caplen et al., PNAS 2000, 98(17): 9742-9747.*
Vickers et al. (J. Biol. Chem., Feb. 2003, 278(9): 7108-7118).*
Katso et al (Annu. Rev. Dev. Biol. 17: 615-675, 2001).*
Knuefermann et al (Oncogene 22: 3205-3212, 2003).*
Okudela et al (Am. J. Pathol. 164(1): 91-100, 2004).*
Leenders et al (EMBO J. 3: 3303-3313, 2004).*
Caplen (Expert Opin. Biol. Ther. 2003, vol. 3, pp. 575-586, 2003).*
Coburn et al.(Journal of Antimicrobial Chemotherapy. vol. 51, pp. 753-756, 2003).*
Agami et al. (Current Opinion in Chemical Biology. vol. 6, pp. 829-834, 2003).*
Opalinska et al. (Nature Reviews Drug Discovery, 2002, vol. 1, pp. 503-514).*
Check (Nature, 2003, vol. 425, pp. 10-12).*
Zhang et al (Current Pharmaceutical Biotechnology 2004, vol. 5, pp. 1-7).*
Agrawal et al (Mol. Med. Today 6:72-81, 2000).*
Lewis et al (Meth. Enzymol. 392, 336-350, 2005).*
Dykxhoorn et al (Ann. Rev. Biomed. Eng. 8: 377-402, 2006).*
Oishi et al (Biochem. Biophys. Res. Comm. 261: 808-814, 1999).*
Iqbal Unnisa Ali, "Gatekeeper for Endometrium: the PTEN Tumor Suppressor Gene", Journal of the National Cancer Institute, Jun. 7, 2000, pp. 861-863, vol. 92, No. 11.
Lewis C. Cantley et al., "New insights into tumor suppression: PTEN suppresses tumor formation by restraining the phosphoinositide 3-kinase/AKT pathway", Proc. Natl. Acad. Sci. USA, Apr. 1999, pp. 4240-4245, vol. 96.
Maria Sternberger et al., "GeneBlocs Are Powerful Tools to Study and Delineate Signal Transduction Processes That Regulate Cell Growth and Transformation", Antisense & Nucleic Acid Drug Development, 2002, pp. 131-143, vol. 12.
Antonio Di Cristofano et al., "Pten is essential for embryonic development and tumour suppression", Nature Genetics, Aug. 19, 1998, vol. 19, pp. 348-355.
Lily Q. Dong et al., "Phosphorylation of protein kinase N by phosphoinositide-dependent protein kinase-1 mediates insulin signals to the actin cytoskeleton", PNAS, May 9, 2000, vol. 97, No. 10, pp. 5089-5094.
Anke Klippel et al., "Activation of Phosphatidylinositol 3-Kinase Is Sufficient for Cell Cycle Entry and Promotes Cellular Changes Characteristic of Oncogenic Transformation", Molecular and Cellular Biology, Oct. 1998, vol. 18, No. 10, pp. 5699-5711.
Michimoto Kobayashi et al., "Dedifferentiation of adenocarcinomas by activation of phosphatidylinositol 3-kinase", Proc. Natl. Acad. Sci. USA, Apr. 1999, vol. 96, pp. 4874-4879.
Yukinobu Maruo et al., "ICAM-1 Expression and the Soluble ICAM-1 Level for Evaluating the Metastatic Potential of Gastric Cancer", Int. J. Cancer: 2002, vol. 100, pp. 486-490.
Kumiko Oishi et al., "Identification and Characterization of PKNβ, a Novel Isoform of Protein Kinase PKN: Expression and Arachidonic Acid Dependency are Different from Those of PKNα", Biochemical and Biophysical Research Communications, 1999, vol. 261, pp. 808-814.

(Continued)

*Primary Examiner*—Richard Schnizer
(74) *Attorney, Agent, or Firm*—Saliwanchik, Lloyd & Saliwanchik

(57) ABSTRACT

The present invention is related to use of protein kinase N beta or a fragment or derivative thereof as a downstream target of the PI 3-kinase pathway, preferably as a downstream drug target of the PI 3-kinase pathway.

32 Claims, 13 Drawing Sheets

OTHER PUBLICATIONS

Ole William Petersen et al., "Interaction with basement membrane serves to rapidly distinguish growth and differentiation pattern of normal and malignant human breast epithelial cells", Proc. Natl. Acad. Sci. USA, Oct. 1992, vol. 89, pp. 9064-9068, Cell Biology.

Dirk Roymans et al., "Phosphatidylinositol 3-kinases in tumor progression", Eur. J. Biochem., 2001, vol. 268, 487-498.

Philip S. Rudland et al., "Prognostic Significance of the Metastasis-associated Protein Osteopontin in Human Breast Cancer", Cancer Research, Jun. 15, 2002, vol. 62, pp. 3417-3427.

Hideki Shibata et al., "PKNβ interacts with the SH3 Domains of Graf and a Novel Graf Related Protein, Graf 2, Which are GTPase Activating Proteins for Rho Family", J. Biochem., 2001, vol. 130, pp. 23-31.

Robert C. Stein et al., "PI3-kinase inhibition: a target for drug development?", Molecular Medicine Today, 2000, vol. 6, pp. 347-357.

Francisca Vazquez et al., Biochimica et Biophysica Acta, 2000, vol. 1470, pp. M21-M35.

Chris J. Vlahost et al., "A Specific Inhibitor of Phosphatidylinositol 3-Kinase, 2-(4-Morpholinyl)-8-phenyl-4H-1-benzopyran-4-one (LY294002)", The Journal of Biological Chemistry, 1994, vol. 269, No. 7, pp. 5241-5248.

K. Yu et al., "mTOR, a novel target in breast cancer: the effect of CCI-779, an MTOR inhibitor, in preclinical models of breast cancer", Endocrine-Related Cancer, 2001, vol. 8, pp. 249-258.

Lewis, D. L. et al. "Efficient delivery of siRNA for inhibition of gene expression in postnatal mice" Nature Genetics, Sep. 2002, pp. 107-108; Web Note A (2 pages) and Web Note B (1 page).

Akhtar, S. et al. "The delivery of antisense therapeutics" Advanced Drug Delivery Reviews, 2000, vol. 44, pp. 3-21.

Opalinska, J.B. et al. "Nucleic-Acid Therapeutics: Basic Principles and Recent Applications" Nature Reviews, 2000, vol. 1, pp. 503-514.

Hoffman, R.M. "Orthotopic metastatic mouse models for anticancer drug discovery and evaluation: a bridge to the clinic" Investigational New Drugs, 1999, vol. 17, pp. 343-359.

Waters, J. S. et al. "Phase I Clinical and Pharmacokinetic Study of Bcl-2 Antisense Oligonucleotide Therapy in Patients with Non-Hodgkin's Lymphoma" J. Clin. Oncol., May 2000, pp. 1812-1823, vol. 18, No. 9.

Chi, K. N. et al. "A Phase I Dose-finding Study of Combined Treatment with an Antisense Bcl-2 Oligonucleotide (Genasense) and Mitoxantrone in Patients with Metastatic Hormone-refractory Prostate Cancer" Clinical Cancer Research, Dec. 2001, pp. 3920-3927, vol. 7.

Nemunaitis, J. et al. "Phase I Evaluation of ISIS 3521, an Antisense Oligodeoxynucleotide to Protein Kinase C-Alpha, in Patients with Advanced Cancer" Journal of Clinical Oncology, Nov. 1999, pp. 3586-3595, vol. 17, No. 11.

Cunningham, C. et al. "A Phase I Trial of H-ras Antisense Oligonucleotide ISIS 2503 Administered as a Continuous Intravenous Infusion in Patients with Advanced Carcinoma" Cancer, 2001, pp. 1265-1271, vol. 92.

Ogris, M. et al. "Targeting tumors with non-viral gene delivery systems" Drug Discovery Today, Apr. 2002, pp. 479-485, vol. 7, No. 8.

Cunningham, C. et al. "A Phase I Trial of c-Raf Kinase Antisense Oligonucleotide ISIS 5132 Administered as a Continuous Intravenous Infusion in Patients with Advanced Cancer" Clinical Cancer Research, May 2000, pp. 1626-1631, vol. 6.

Yuen, A. R. et al. "Phase I Study of an Antisense Oligonucleotide to Protein Kinase C-α (ISIS 3521/CGP 64128A) in Patients with Cancer" Clinical Cancer Research, Nov. 1999, pp. 3357-3363, vol. 5.

Devroe, E. et al. "Retrovirus-delivered siRNA" BMC Biotechnology, 2002, pp. 1-5, vol. 2.

Yacyshyn, B.R. et al. "A Placebo-Controlled Trial of ICAM-1 Antisense Oligonucleotide in the Treatment of Crohn's Disease" Gastroenterology, 1998, pp. 1133-1142, vol. 114.

Jansen, B. et al. "Chemosensitisation of malignant melanoma by BCL2 antisense therapy" The Lancet, Nov. 18, 2000, pp. 1728-1733, vol. 326.

Aleku, M. et al. "Atu027, a Liposomal Small Interfering RNA Formulation Targeting Protein Kinase N3, Inhibits Cancer Progression" Cancer Res, Dec. 2, 2008, pp. 9788-9798 and supplementary content, vol. 68, No. 23.

Lewis, et al. "Delivery of siRNA and siRNA Expression Constructs to Adult Mammals by Hydrodynamic Intravascular Injection" Methods of Enzymology, 2005, pp. 336-350, vol. 392.

Lu, Y. et al. "The Drosophila Pkn protein kinase is a Rho/Rac effector target required for dorsal closure during embryogenesis" Genes Dev., 1999, pp. 1168-1180, vol. 13.

Mukai, H. "The Structure and Function of PKN, a Protein Kinase Having a Catalytic Domain Homologous to That of PKC" J. Biochem., 2003, pp. 17-27, vol. 133.

Su, C. et al. "PKN Activation via Transforming Growth Factor-β1 (TGF-β1) Receptor Signaling Delays $G_2$/M Phase Transition in Vascular Smooth Muscle Cells" Cell Cycle, Mar. 15, 2007, pp. 739-749, vol. 6, No. 6.

Metzger, E. et al. "A novel inducible transactivation domain in the androgen receptor: implications for PRK in prostate cancer" The EMBO Journal, 2003, pp. 270-280, vol. 22, No. 2.

Dong, L. Q. et al. "Phosphorylation of protein kinase N by phosphoinositide-dependent protein kinase-1 mediates insulin signals to the actin cytoskeleton" PNAS, May 9, 2000, pp. 5089-5094, vol. 97, No. 10.

Fischer, A. et al. "Impaired tight junction sealing and precocious involution in mammary glands of PKN1 transgenic mice" Journal of Cell Science, 2007, pp. 2272-2283, vol. 120.

Flynn, P. et al. "Rho GTPase Control of Protein Kinase C-related Protein Kinase Activation by 3-Phosphoinositide-dependent Protein Kinase" The Journal of Biological Chemistry, Apr. 14, 2000, pp. 11064-11070, vol. 275, No. 15.

Manning, G. et al. "The Protein Kinase Complement of the Human Genome" Science, 2002, pp. 1912-1934, vol. 298.

Kaufmann, J. et al. "Identification of novel effectors of invasive cell growth downstream of phosphoinositide 3-kinase" Biochemical Society Transactions, 2004, pp. 355-359, vol. 32, Part 2.

Mukai, H. et al. "Purification and Kinase Assay of PKN" Methods in Enzymology, 2006, pp. 234-250, vol. 406.

Leenders, F. et al. "PKN3 is required for malignant prostate cell growth downstream of activated PI 3-kinase" The EMBO Journal, 2004, pp. 3303-3313, vol. 23, No. 16, XP-002459350.

Leenders, F. et al. "PKN3 is required for malignant prostate cell growth downstream of activated phosphatidylinositol 3-kinase" EMBO Journal, Supplementary Information Section, 2004, pp. 1-23, XP-002459351.

Section "Kolorektale Adenome, Adenomkrankhelt, Polypen" Thiemes Innere Medizin, 1999, pp. 1-6.

Entry "lipoma" from Stedman's Medical Dictionary, The Williams & Wilkins Company, Baltimore, 1996, pp. 1-4.

Entry "Trichilemmom" from Zetkin, M. and Schaldach, H., Worterbuch der Medizin, Ullstein Mosby, Berlin, 1992, pp. 1-3.

Pending claims in U.S. Appl. No. 12/307,052, filed Apr. 15, 2009.

* cited by examiner

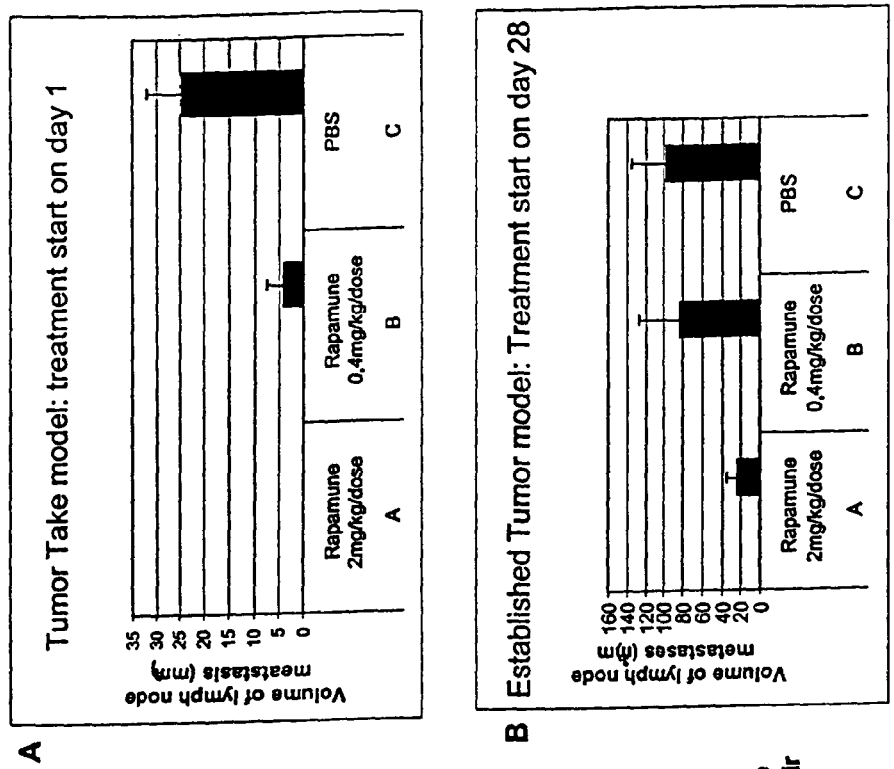
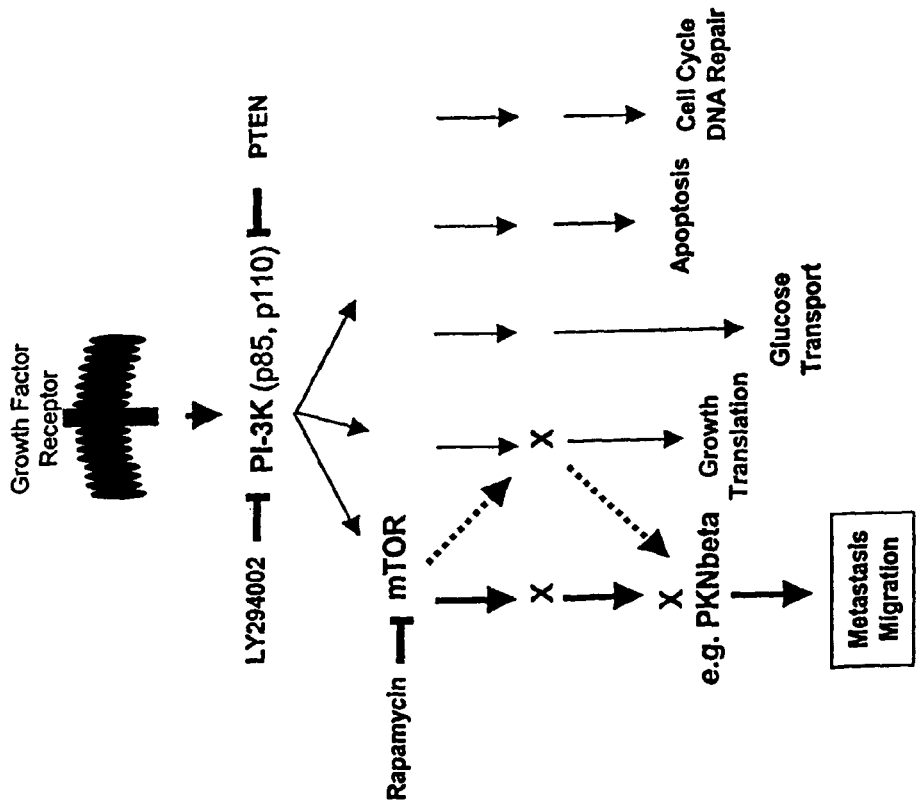
Fig. 2
Fig. 1

A. Expression of recombinant "KINASE" Western blot atugen antibody
anti-"KINASE"

B. In Vivo Phosphorylation of recombinant "KINASE"

anti P*-AGC Kinase

Homology to AGC-Family of Kinase Molecules

FL, Full length "KINASE"
KD, "KINASE" domain
FL$_{KE}$; mutation Lys→Glu in "KINASE" domain
FL$_{TA}$, mutation Thr→Ala in activation loop

Anti-Myc tag Immunoprecipitation/In Vitro Kinase Assay:

A. Non-Radioactive

| | $FL_{wt}$ | KD | $FL_{KE}$ | $FL_{TA}$ |
|---|---|---|---|---|
| #1 | 3 | 1 2 | 5 6 | 7 8 |

Western-blot

In Vitro Phosphorylated Substrate

B. Radioactive

| | $FL_{wt}$ | KD | $FL_{KE}$ | $FL_{TA}$ |
|---|---|---|---|---|
| #1 | 3 | 1 2 | 5 6 | 7 8 |

*

Autoradiography [$^{32}$P] incorporation
In Vitro Phosphorylated Substrate

C. Immunoblot analysis of IP

| | $FL_{wt}$ | KD | $FL_{KE}$ | $FL_{TA}$ |
|---|---|---|---|---|
| #1 | 3 | 1 2 | 5 6 | 7 8 |

*

** atugen antibody
anti "KINASE"

SEQUENCE LISTING

<160> NUMBER OF SEQ ID NOS: 18

<210> SEQ ID NO 1
<211> LENGTH: 889
<212> TYPE: PRT
<213> ORGANISM: Homo sapiens

<400> SEQUENCE: 1

Met Glu Glu Gly Ala Pro Arg Gln Pro Gly Ser Gln Trp Pro Pro
 1               5                  10                  15

Glu Asp Glu Lys Glu Val Ile Arg Arg Ala Ile Gln Lys Glu Leu Lys
            20                  25                  30

Ile Lys Glu Gly Val Glu Asn Leu Arg Arg Val Ala Thr Asp Arg Arg
        35                  40                  45

His Leu Gly His Val Gln Gln Leu Leu Arg Ser Ser Asn Arg Arg Leu
    50                  55                  60

Glu Gln Leu His Gly Glu Leu Arg Glu Leu His Ala Arg Ile Leu Leu
65                  70                  75                  80

Pro Gly Pro Gly Pro Gly Pro Ala Glu Pro Val Ala Ser Gly Pro Arg
                85                  90                  95

Pro Trp Ala Glu Gln Leu Arg Ala Arg His Leu Glu Ala Leu Arg Arg
            100                 105                 110

Gln Leu His Val Glu Leu Lys Val Lys Gln Gly Ala Glu Asn Met Thr
        115                 120                 125

His Thr Cys Ala Ser Gly Thr Pro Lys Glu Arg Lys Leu Leu Ala Ala
    130                 135                 140

Ala Gln Gln Met Leu Arg Asp Ser Gln Leu Lys Val Ala Leu Leu Arg
145                 150                 155                 160

Met Lys Ile Ser Ser Leu Glu Ala Ser Gly Ser Pro Glu Pro Gly Pro
                165                 170                 175

Glu Leu Leu Ala Glu Glu Leu Gln His Arg Leu His Val Glu Ala Ala
            180                 185                 190

Val Ala Glu Gly Ala Lys Asn Val Val Lys Leu Leu Ser Ser Arg Arg
        195                 200                 205

Thr Gln Asp Arg Lys Ala Leu Ala Glu Ala Gln Ala Gln Leu Gln Glu
    210                 215                 220

Ser Ser Gln Lys Leu Asp Leu Leu Arg Leu Ala Leu Glu Gln Leu Leu
225                 230                 235                 240

Glu Gln Leu Pro Pro Ala His Pro Leu Arg Ser Arg Val Thr Arg Glu
                245                 250                 255

Leu Arg Ala Ala Val Pro Gly Tyr Pro Gln Pro Ser Gly Thr Pro Val
            260                 265                 270

Lys Pro Thr Ala Leu Thr Gly Thr Leu Gln Val Arg Leu Leu Gly Cys
        275                 280                 285

Glu Gln Leu Leu Thr Ala Val Pro Gly Arg Ser Pro Ala Ala Ala Leu
    290                 295                 300

Ala Ser Ser Pro Ser Glu Gly Trp Leu Arg Thr Lys Ala Lys His Gln
305                 310                 315                 320

Arg Gly Arg Gly Glu Leu Ala Ser Glu Val Leu Ala Val Leu Lys Val
                325                 330                 335

Asp Asn Arg Val Val Gly Gln Thr Gly Trp Gly Gln Val Ala Glu Gln
            340                 345                 350

Ser Trp Asp Gln Thr Phe Val Ile Pro Leu Glu Arg Ala Arg Glu Leu

-continued

```
                355                 360                 365
Glu Ile Gly Val His Trp Arg Asp Trp Arg Gln Leu Cys Gly Val Ala
    370                 375                 380
Phe Leu Arg Leu Glu Asp Phe Leu Asp Asn Ala Cys His Gln Leu Ser
385                 390                 395                 400
Leu Ser Leu Val Pro Gln Gly Leu Leu Phe Ala Gln Val Thr Phe Cys
                405                 410                 415
Asp Pro Val Ile Glu Arg Arg Pro Arg Leu Gln Arg Gln Glu Arg Ile
                420                 425                 430
Phe Ser Lys Arg Arg Gly Gln Asp Phe Leu Arg Ser Gln Met Asn
            435                 440                 445
Leu Gly Met Ala Ala Trp Gly Arg Leu Val Met Asn Leu Leu Pro Pro
    450                 455                 460
Cys Ser Ser Pro Ser Thr Ile Ser Pro Pro Lys Gly Cys Pro Arg Thr
465                 470                 475                 480
Pro Thr Thr Leu Arg Glu Ala Ser Asp Pro Ala Thr Pro Ser Asn Phe
                485                 490                 495
Leu Pro Lys Lys Thr Pro Leu Gly Glu Glu Met Thr Pro Pro Lys
            500                 505                 510
Pro Pro Arg Leu Tyr Leu Pro Gln Glu Pro Thr Ser Glu Glu Thr Pro
                515                 520                 525
Arg Thr Lys Arg Pro His Met Glu Pro Arg Thr Arg Arg Gly Pro Ser
    530                 535                 540
Pro Pro Ala Ser Pro Thr Arg Lys Pro Arg Leu Gln Asp Phe Arg
545                 550                 555                 560
Cys Leu Ala Val Leu Gly Arg Gly His Phe Gly Lys Val Leu Leu Val
                565                 570                 575
Gln Phe Lys Gly Thr Gly Lys Tyr Tyr Ala Ile Lys Ala Leu Lys Lys
            580                 585                 590
Gln Glu Val Leu Ser Arg Asp Glu Ile Glu Ser Leu Tyr Cys Glu Lys
                595                 600                 605
Arg Ile Leu Glu Ala Val Gly Cys Thr Gly His Pro Phe Leu Leu Ser
    610                 615                 620
Leu Leu Val Cys Phe Gln Thr Ser Ser His Ala Arg Phe Val Thr Glu
625                 630                 635                 640
Phe Val Pro Gly Gly Asp Leu Met Met Gln Ile His Glu Asp Val Phe
                645                 650                 655
Pro Glu Pro Gln Ala Arg Phe Tyr Val Ala Cys Val Val Leu Gly Leu
                660                 665                 670
Gln Phe Leu His Glu Lys Lys Ile Ile Tyr Arg Asp Leu Lys Leu Asp
            675                 680                 685
Asn Leu Leu Leu Asp Ala Gln Gly Phe Leu Lys Ile Ala Asp Phe Gly
    690                 695                 700
Leu Cys Lys Glu Gly Ile Gly Phe Gly Asp Arg Thr Ser Thr Phe Cys
705                 710                 715                 720
Gly Thr Pro Glu Phe Leu Ala Pro Glu Val Leu Thr Gln Glu Ala Tyr
                725                 730                 735
Thr Gln Ala Val Asp Trp Trp Ala Leu Gly Val Leu Leu Tyr Glu Met
            740                 745                 750
Leu Val Gly Glu Cys Pro Phe Pro Gly Asp Thr Glu Glu Val Phe
            755                 760                 765
Asp Cys Ile Val Asn Met Asp Ala Pro Tyr Pro Gly Phe Leu Ser Val
    770                 775                 780
```

```
Gln Gly Leu Glu Phe Ile Gln Lys Leu Leu Gln Lys Cys Pro Glu Lys
785                 790                 795                 800

Arg Leu Gly Ala Gly Glu Gln Asp Ala Glu Glu Ile Lys Val Gln Pro
                805                 810                 815

Phe Phe Arg Thr Thr Asn Trp Gln Ala Leu Leu Ala Arg Thr Ile Gln
            820                 825                 830

Pro Pro Phe Val Pro Thr Leu Cys Gly Pro Ala Asp Leu Arg Tyr Phe
        835                 840                 845

Glu Gly Glu Phe Thr Gly Leu Pro Pro Ala Leu Thr Pro Pro Ala Pro
    850                 855                 860

His Ser Leu Leu Thr Ala Arg Gln Gln Ala Ala Phe Arg Asp Phe Asp
865                 870                 875                 880

Phe Val Ser Glu Arg Phe Leu Glu Pro
                885
```

<210> SEQ ID NO 2
<211> LENGTH: 2670
<212> TYPE: DNA
<213> ORGANISM: Homo sapiens

<400> SEQUENCE: 2

| | | | | | |
|---|---|---|---|---|---|
| atggaggagg | gggcgccgcg | gcagcctggg | ccgagccagt | ggcccccaga | ggatgagaag | 60 |
| gaggtgatcc | gccgggccat | ccagaaagag | ctgaagatca | aggagggggt | ggagaacctg | 120 |
| cggcgcgtgg | ccacagaccg | ccgccacttg | ggccatgtgc | agcagctgct | gcggtcctcc | 180 |
| aaccgccgcc | tggagcagct | gcatggcgag | ctgcgggagc | tgcacgcccg | aatcctgctg | 240 |
| cccggccctg | ggcctggccc | agctgagcct | gtggcctcag | accccggcc | gtgggcagag | 300 |
| cagctcaggg | ctcggcacct | agaggctctc | cggaggcagc | tgcatgtgga | gctgaaggtg | 360 |
| aaacagggg | ctgagaacat | gacccacacg | tgcgccagtg | gcaccccaa | ggagaggaag | 420 |
| ctccttgcag | ctgcccagca | gatgctgcgg | gacagcagc | tgaaggtggc | cctgctgcgg | 480 |
| atgaagatca | gcagcctgga | ggccagtggg | tccccggagc | cagggcctga | gctactggcg | 540 |
| gaggagctac | agcatcgact | gcacgttgag | gcagcggtgg | ctgagggcgc | caagaacgtg | 600 |
| gtgaaactgc | ttagtagccg | gagaacacag | gaccgcaagg | cactggctga | ggcccaggcc | 660 |
| cagctacagg | agtcctctca | gaaactggac | ctcctgcgcc | tggccttgga | gcagctgctg | 720 |
| gagcaactgc | tcctgcccca | ccctttgcgc | agcagagtga | cccgagagtt | gcgggctgcg | 780 |
| gtgcctggat | accccagcc | ttcagggaca | cctgtgaagc | ccaccgccct | aacagggaca | 840 |
| ctgcaggtcc | gcctcctggg | ctgtgaacag | ttgctgacag | ccgtgcctgg | gcgctcccca | 900 |
| gcggccgcac | tggccagcag | ccctccgag | ggctggcttc | ggaccaaggc | caagcaccag | 960 |
| cgtggccgag | gcgagcttgc | cagtgaggtg | ctggctgtgc | taaaggtgga | caaccgtgtt | 1020 |
| gtggggcaga | cggctgggg | gcaggtggcc | gaacagtcct | gggaccagac | ctttgtcatc | 1080 |
| ccactggagc | gagcccgtga | gctggagatt | ggggtacact | ggcgggactg | gcggcagcta | 1140 |
| tgtgccgtgg | ccttcctgag | acttgaagac | ttcctggaca | tgcctgtca | ccaactgtcc | 1200 |
| ctcagcctgg | taccgcaggg | actgcttttt | gccaggtga | ccttctgcga | tcctgtcatt | 1260 |
| gagaggcggc | cccggctgca | gaggcaggaa | cgcatcttct | ctaaacgcag | aggccaggac | 1320 |
| ttcctgaggc | gttcgcagat | gaacctcggc | atggcggcct | gggggcgcct | cgtcatgaac | 1380 |
| ctgctgcccc | cctgcagctc | cccgagcaca | atcagccccc | ctaaaggatg | ccctcggacc | 1440 |
| ccaacaacac | tgcgagaggc | ctctgaccct | gccactccca | gtaatttcct | gcccaagaag | 1500 |

-continued

```
accccctteg gtgaagagat gacacccca cccaagcccc cacgcctcta cctcccccag    1560
gagccaacat ccgaggagac tccgcgcacc aaacgtcccc atatggagcc taggactcga    1620
cgtgggccat ctccaccagc ctcccccacc aggaaacccc ctcggcttca ggacttccgc    1680
tgcttagctg tgctgggccg gggacacttt gggaaggtcc tcctggtcca gttcaagggg    1740
acagggaaat actacgccat caaagcactg aagaagcagg aggtgctcag ccgggacgag    1800
atagagagcc tgtactgcga aagcggatc ctggaggctg tgggctgcac agggcaccct    1860
ttcctgctct ccctccttgt ctgcttccag acctccagcc atgcccgctt tgtgactgag    1920
tttgtgcctg gtggtgacct catgatgcag atccacgagg atgtcttccc cgagccccag    1980
gcccgcttct acgtggcttg tgttgtcctg gggctgcagt tcttacacga aagaagatc    2040 atttacaggg acctgaagtt ggataacctt ctgctggatg cccagggatt cctgaagatc    2100
gcagactttg gactctgcaa ggaagggatc ggcttcgggg accggactag caccttctgt    2160
ggcaccccgg agttcctggc tcccgaggtg ctgacccagg aggcatacac acaggccgtc    2220
gactggtggg cgctgggtgt gctgctctac gagatgctgg tgggtgagtg cccgttccca    2280
ggggacacag aggaagaggt gtttgactgc atcgtcaaca tggacgcccc ctaccccggc    2340
tttctgtcgg tgcaagggct tgagttcatt cagaagctcc tccagaagtg cccggagaag    2400
cgcctcgggg caggtgagca ggatgccgag gagatcaagg tccagccatt cttcaggacc    2460
accaactggc aagccctgct cgcccgcacc atccagcccc ccttcgtgcc taccctgtgt    2520
ggccctgcgg acctgcgcta ctttgagggc gagttcacag gctgccgcc tgccctgacc    2580 ccacctgcac cccacagcct cctcactgcc cgccaacagg ccgccttccg ggacttcgac    2640
tttgtgtcag agcgattcct ggaaccctga                                     2670
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ggagguccag tttctgagag g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
uguuucaccu ucagcuccac a                                              21

<210> SEQ ID NO 5
<211> LENGTH: 23
<212> TYPE: DNA
<213> ORGANISM: Artificial Sequence
<220> FEATURE:
```

<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
aggacaacac aagccacgua gaa                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
gcucugacac aaagtcgaag ucc                                          23

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
gcagucaaac acctctuccu cug                                          23

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
caacacggtt gtccaccuuu a                                            21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ucagugcttt gatggcguag u                                            21

<210> SEQ ID NO 10
<211> LENGTH: 21
<212> TYPE: DNA
<213> ORGANISM: Artificial Sequence

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
cuucucgcag tacaggcucu c                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
caagacgctt gtgcacguuu a                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
ucagagctta gttggcguug u                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actgagcaag aggctttgga g                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aaattccagt ggttcattcc a                                              21

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
```

```
<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggaatgaac cactggaata gcaaaaaaaa aaaagcttcc agtggttcat tccc           54

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctctcagaaa ctggacctcc taaaaaaaaa aaaaggaggt ccagtttctg agag           54

<210> SEQ ID NO 18
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tcactgtaaa gctggaaagg gaaaaaaaaa aaaaggaggt ccagtttctg agag           54
```

FURTHER USE OF PROTEIN KINASE N BETA

FIELD OF THE INVENTION

The invention provides compositions and methods related to the use of protein kinase N beta.

BACKGROUND OF THE INVENTION

Modern drug development no longer relies on a more or less heuristic approach but typically involves the elucidation of the molecular mechanisms underlying a disease or a condition, the identification of candidate target molecules and the evaluation of said target molecules. Once such a validated target molecule, which is herein referred to also as target, is available, drug candidates directed thereto may be tested. In many cases such drug candidates are members of a compound library which may consist of synthetic or natural compounds. Also the use of combinatorial libraries is common. Such compound libraries are herein also referred to as candidate compound libraries. Although in the past this approach has proven to be successful, it is still time and money consuming. A variety of technologies currently are applied for target identification and target validation.

Still, numerous tumours and cancers pose a significant threat to human health. In order to create safer and more powerful drugs having less side effects, it is necessary to identify target molecules which, upon being addressed by appropriate compounds, may specifically and selectively be influenced in their activity or presence. Because of the preferably selective and specific interaction between the compound, which may be a potential or candidate drug, and the target, the target's function in a disease or diseased condition such as, for example, cancer, tumorigenesis and metastasis, may be influenced and thus the disease treated or prevented and the diseased condition ameliorated.

It is apparent that new targets suitable for development of new therapeutic approaches in the treatment of tumorigenesis and cancer are greatly to be desired. It also is apparent that new methods of therapeutic intervention directed at those targets are greatly to be desired.

SUMMARY OF THE INVENTION

It is therefore an object of the invention to provide new targets for therapeutic invention and the treatment of disease. It is a further object of the invention to provide compositions and methods suitable for therapeutic intervention against these new targets.

In accordance with these objects, there has been provided, in accordance with a first aspect of the invention, the use of protein kinase N beta or a fragment or derivative thereof as a downstream target of the PI 3-kinase pathway, preferably as a downstream drug target of the PI 3-kinase pathway.

In accordance with a second aspect of the invention there are provided compositions and methods for using protein kinase N beta or a fragment or derivative thereof for the manufacture of a medicament for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway.

In an embodiment of the use according to the first and second aspect of the present invention protein kinase N beta has an amino acid sequence according to SEQ ID NO. 1 or according to databank entry PID g7019489 or databank entry gi 7019489, or a part or derivative thereof.

In accordance with a third aspect of the invention there is provided a use of a nucleic acid coding for protein kinase N beta, or a fragment or a derivative thereof for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway.

In an embodiment of the use according to the third aspect of the present invention protein kinase N beta has an amino acid sequence according to SEQ ID NO. 1 or according to databank entry PID g7019489 or databank entry gi 7019489, or a part or derivative thereof.

In another embodiment of the use according to the third aspect of the present invention the nucleic acid is a nucleic acid according to SEQ ID NO. 2 or according to databank entries gi 7019488 or NM_01335, preferably NM_01335.1.

In another embodiment of the use according to the any of the aspects of the present invention protein kinase N beta is coded by a nucleic acid according to SEQ ID NO. 2 or according to databank entries gi 7019488 or NM_01335, preferably NM_01335.1.

In a preferred embodiment of the use according to the third aspect of the present invention the nucleic acid sequence, but for the degeneracy of the genetic code, would hybridize to the inventive nucleic acid subject to the third aspect of the present invention.

In a further embodiment of the use according to the any of the aspects of the present invention the nucleic acid sequence is a sequence which hybridizes under stringent conditions to the nucleic acid sequence or part thereof, according to SEQ ID NO. 2 or according to databank entries gi 7019488 or NM_01335, preferably NM_01335.1.

In a preferred embodiment of the use according to any of the aspects of the present invention the disease is characterized such that the cells being involved in said disease, lack PTEN activity, show an increased aggressive behaviour, or are cells of a late stage tumor.

In another preferred embodiment of the use according to the third aspect of the present invention the disease is a late stage tumor.

In accordance with another aspect of the invention there is provided a method for the screening of an agent for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway comprising the steps:

a) providing a candidate compound, b) providing an expression system for protein kinase N beta and/or a system detecting the activity of protein kinase N beta;

c) contacting of the candidate compound with the expression system for protein kinase N beta and/or the system detecting activity of protein kinase N beta;

d) determining if the expression and/or the activity of protein kinase N beta is changed under the influence of the candidate compound.

In an embodiment of the method according to the fourth aspect of the present invention the candidate compound is contained in a library of compounds.

In another embodiment of the method according to the fourth aspect of the present invention the candidate compound is selected from the group of classes of compounds comprising peptides, proteins, antibodies, anticalines, functional nucleic acids, natural compounds and small molecules.

In a preferred embodiment of the method according to the fourth aspect of the present invention the functional nucleic acids are selected from the group which comprises aptamers, aptazymes, ribozymes, spiegelmers, antisense oligonucleotides and siRNA.

In a further preferred embodiment of the method according to the fourth aspect of the present invention protein kinase N beta or the nucleic acid coding for protein kinase N beta are the ones described in connection with any other aspect of the present invention.

In accordance with a fifth aspect of the invention there is provided the use of protein kinase N beta or a part or derivative thereof and/or nucleic acid or a part or derivative thereof coding for protein kinase N beta as target molecule for the development and/or manufacture of a medicament for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway.

In an embodiment of the use according to the fifth aspect of the present invention the medicament and/or the diagnostic agent comprises an agent, which is selected from the group comprising antibodies, peptides, anticalines, small molecules, antisense molecules, aptameres, spiegelmers and RNAi molecules.

In a preferred embodiment of the use according to the fifth aspect of the present invention the agent interacts with the protein kinase N beta or a part or derivative thereof.

In an alternative embodiment of the use according to the fifth aspect of the present invention the agent interacts with the nucleic acid coding for protein kinase N beta or a part or derivative thereof, in particular with MRNA, genomic nucleic acid or cDNA for protein kinase N beta.

In accordance with a sixth aspect of the invention there is provided the use of a polypeptide which interacts with protein kinase N beta or a part or derivative thereof, for the development or manufacture of a medicament for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway.

In an embodiment of the use according to the sixth aspect of the present invention the polypeptide is selected from the group which comprises antibodies against protein kinase N beta or a part or derivative thereof and polypeptides binding protein kinase N beta or a part or derivative thereof.

In accordance with a seventh aspect of the invention there is provided the use of a nucleic acid which interacts with protein kinase N beta or a part or derivative thereof, for the development or manufacture of a medicament for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway.

In an embodiment of the use according to the seventh aspect of the present invention the nucleic acid is selected from the group which comprises aptamers and spiegelmers.

In accordance with an eighth aspect of the invention there is provided the use of a nucleic acid which interacts with a nucleic acid coding for protein kinase N beta or a part or derivative thereof, for the development or manufacture of a medicament for the treatment and/or prevention of a disease and/or for the manufacture of a diagnostic agent for the diagnosis of a disease, whereby the disease is selected from the group comprising cancers, metastatic cancers and any pathological conditions involving the PI 3-kinase pathway.

In an embodiment of the use according to the eighth aspect of the present invention the interacting nucleic acid is an antisense oligonucleotide, a ribozyme and/or siRNA.

In a further embodiment of the use according to the eighth aspect of the present invention the nucleic acid coding for protein kinase N beta or a part or derivative thereof is the cDNA, mRNA or hnRNA.

In an embodiment of the use according to the eighth aspect of the present invention the protein kinase N beta and/or the nucleic acid coding for protein kinase N beta is the one described in connection with any aspect of the present invention.

In accordance with a ninth aspect of the invention there is provided a pharmaceutical composition comprising at least one agent selected from the group comprising protein kinase N beta or a part or derivative thereof, small molecules interacting with protein kinase N beta or a part or derivative thereof or with a nucleic acid coding for protein kinase N beta or a part or derivative thereof, antibodies specific for protein kinase N beta or a part or derivative thereof, polypeptides interacting with protein kinase N beta or a part or derivative thereof, a nucleic acid coding for protein kinase N beta or a part or derivative thereof, nucleic acids interacting with protein kinase N beta or a part or derivative thereof or nucleic acids interacting with a nucleic acid coding for protein kinase N beta or a part or derivative thereof, and at least one pharmaceutically acceptable carrier, preferably for the prevention and/or the treatment of a disease whereby the disease is selected from the group comprising cancers, metastatic cancers and any pathological conditions involving the PI-3 kinase pathway.

In accordance with a stenth aspect of the invention there is provided a kit for the characterisation of a disease or a condition which is selected from the group comprising cancers, metastatic cancers and any pathological conditions involving the PI-3 kinase pathway, comprising at least one agent which is selected from the group comprising protein kinase N beta or a part or derivative thereof, antibodies specific for protein kinase N beta or a part or derivative thereof, polypeptides interacting with protein kinase N beta or a part or derivative thereof, polypeptides interacting with a nucleic acid coding for protein kinase N beta or a part or derivative thereof, nucleic acids interacting with protein kinase N beta or a part or derivative thereof, nucleic acids interacting with a nucleic acid coding for protein kinase N beta or a part or derivative thereof, and optionally at least one other compound.

BRIEF DESCRIPTION OF THE DRAWINGS

The present invention is now further illustrated by the following figures and examples which are not intended to limit the scope of protection. From these figures and examples further features, embodiments and advantages may be taken, wherein FIG. 1 shows a schematic representation of growth factor induced activation of the PI 3-kinase pathway. Growth factor stimulation of cells leads to activation of their cognate receptors at the cell membrane, which in turn associate with and activate intracellular signalling molecules such as PI 3-kinase. The tumor suppressor PTEN interferes with PI 3-kinase mediated downstream responses and ensures that activation of the pathway occurs in a transient manner. LY294002 is a small molecule inhibitor of PI 3-kinase. One of the known downstream genes of PI 3-K is mTOR (mammalian target of Rapamycin) which can be inhibited by the clinically approved drug rapamycin (Rapamune). PI 3-K is involved in the regulation of cell proliferation, cell survival, glucose transport, translation, metastasis and migration. X are indicating downstream effectors which represent potential drug targets that are predicted to be involved in promoting metastatic behavior of cancer cells. This class of effector molecules which act further downstream in the pathway are likely to represent better drug targets than more "upstream" targets such as mTOR, since they have fewer pleiotropic effects.

FIG. 2 shows the measurement of lymph node metastasis in an orthotopic PC-3 mouse model after treatment on day 1 (2A) and on day 28 (2B) of treatment with rapamycin;

FIG. 11 shows the results of immunoprecipitation assays to detect phosphorylation of protein substrates for protein kinase N beta detecting the phosphorylated form thereof by Western blotting (FIG. 11A) or the incorporation of $^{32}$P-labelled phosphate by autoradiography (FIG. 11B). To ensure that comparable amounts of PKNbeta were present in the respective immune precipitates the filter shown in FIG. 11A was reprobed using an anti-PKNbeta antibody ("kinase", FIG. 11C).

DETAILED DESCRIPTION

Figure 3:
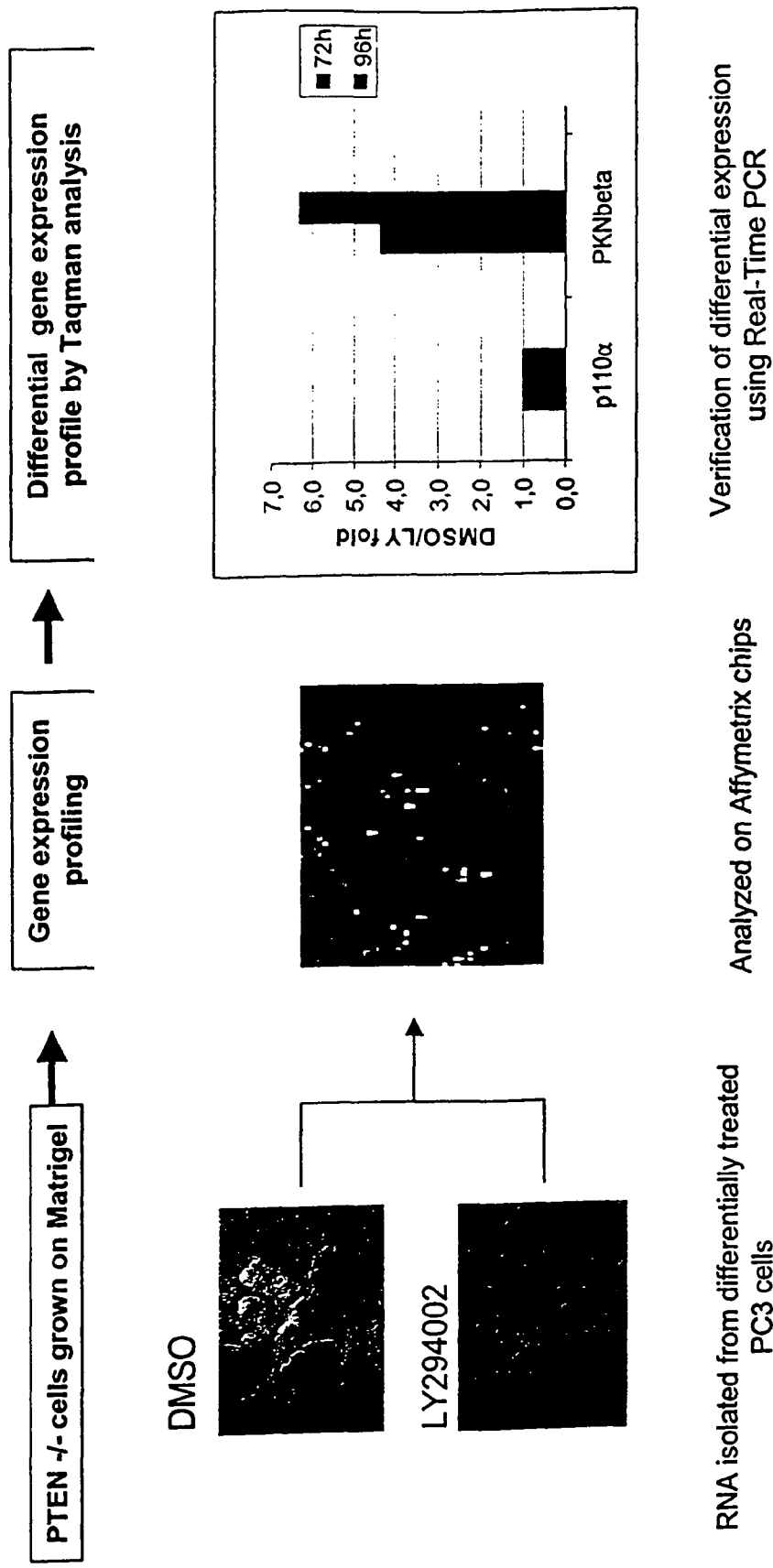
FIG. 3 shows the experimental approach to identify PKN-beta as a downstream drug target of the PI 3-Kinase pathway.

The present inventors have surprisingly found that protein kinase N beta, also referred to herein as PKN beta, is a valuable target in connection with cancer and tumours. More particularly, the present inventors have discovered that protein kinase N beta is a downstream target of the PI-3 kinase/PTEN pathway. Still more surprisingly the present inventors have discovered that protein kinase N beta is linked to tumorigenesis and metastasis.

This latter effect in particular seems to be strongly related to the loss of suppressor function, more particularly PTEN tumour suppressor function. As will be shown in the examples, protein kinase N beta is up-regulated under conditions where PTEN which is an inhibitor to the PI-3 kinase pathway, is not active. Cells in which up-regulation of protein kinase N beta occurs show an increase in metastatic behaviour and migrational behaviour. This means that inhibitors of protein kinase N beta can be used to control metastatic and migrational behaviour of cells and therefore provide methods of treating tumors and cancers, more particularly those tumors and cancers which are metastatic and the cells of which show a metastatic and/or migrational behaviour which are generally referred to herein as 'the disease as described herein' or as 'diseased condition as described herein'.

The disease as described herein as well as the diseased condition as described herein also includes tumorigenesis and metastasis. This applies particularly to those diseases as described herein and those diseased conditions as described herein, where the cells involved in such diseases or diseased conditions are PTEN negative which means that the tumor suppressor PTEN is not active or has a reduced level of activity. The diseases also comprise those diseases in which the PI 3-kinase pathway is in general involved.

Besides metastatic tumors in particular, diabetes falls within this kind of diseases and diseased condition, respectively. Accordingly, cells, particularly those which are involved in the disease or diseased condition as described herein and which are PTEN negative, may be treated by a drug that reduces or eliminates the activity of protein kinase N beta in the respective cells involved. Accordingly, patients whose tumors are characterized by a preferably hyperactivated PI 3-kinase pathway, including but not limited to, either through amplification or mutation of genes encoding components of the PI 3-kinase pathway (p110, Akt) or are PTEN negative or who have cells which are PTEN negative, particularly if these cells are involved in the disease as described herein or in the diseased condition as described herein, can advantageously be treated using said drugs.

The reduction in activity may stem either from a reduction at the transcription level or at the level of the translation, i.e. the enzymatic activity of protein kinase N beta. Without wishing to be bound by any theory, the latter aspect, i.e. modifying the activity of the protein kinase N beta is also a result from an insight of the inventors in relation to the characteristics of PKNbeta, namely that the enzymatic activity of PKNbeta can also be up- and down-regulated, more preferably down-regulated.

A further group of patients who can advantageously be treated using these drugs are those who suffer from cancers which have a high incidence for loss of PTEN function, especially in late stage tumors (Cantley, L. C. and Neel, B. G. (1999). New insights into tumor suppression: PTEN suppresses tumor formation by restraining the phosphoinositide 3-kinase/AKT pathway. *Proc Natl Acad Sci USA* 96, 4240-4245; Ali, I. U. (2000). Gatekeeper for endometrium: the PTEN tumor suppressor gene. *J Natl Cancer Inst* 92, 861-863). Loss of PTEN correlates with increased aggressive and invasive behavior of the respective tumor cells. Because of this, in preferred embodiments of the present invention those diagnostic agents which may also be used as analytical tools or means in connection with the various aspects of the present invention, and therapeutic agents, respectively, directed to protein kinase N beta or nucleic acids coding therefore, can be used for any tumor provided that the aforementioned prerequisite is met, namely that PTEN correlates with increased aggressive and invasive behaviour.

This kind of drug may be designed, screened or manufactured on the basis of the disclosure given herein, namely that protein kinase N beta is a downstream drug target and that protein kinase N beta is a target for tumorigenesis and metastasis and diseases related thereto or arising therefrom.

Because of the involvement of protein kinase N beta in the mechanisms as outlined above, it can also be used as a marker for diagnosing the status of a cell or patient having in his body such kind of cells whether it will undergo metastasis and tumorigenesis, respectively. An illustration that this kind of approach works and is applicable for that purpose is, e.g., ICAM-1. ICAM-1 is used in the prognosis of gastric cancers to undergo metastasis (Maruo Y, Gochi A, Kaihara A, Shimamura H, Yamada T, Tanaka N, Orita K.*Int J Cancer.* 2002 Aug. 1;100(4):486-490) where s-ICAM-1 levels were found to be elevated in pateinets with liver metasasis. In another example, osteopontin is used as a prognostic marker for breast cancer (Rudland P S, Platt-Higgins A, El-Tanani M, De Silva Rudland S, Barraclough R, Winstanley J H, Howitt R, West C R. *Cancer Res.* 2002 Jun. 15;62(12):3417-3427). In so far the presence or the level of presence (protein or mRNA) or the level of activity of protein kinase N beta may be used as a marker and any compound more or less specifically interacting with protein kinase N beta will therefore be an appropriate diagnostic agent.

Methods and design principles for drugs and diagnostic agents which in any case specifically and/or selectively interact with protein kinase N beta will be disclosed in the following.

In the light of these findings kinase N beta proves to be a suitable downstream drug target which allows the selective modulation of only some aspects which are typically related to PI-3 kinase pathway, namely metastasis and migration, and a selective and specific diagnostic approach, i.e. detection, of processes typically related to a dysregulated PI 3-kinase pathway, more particularly metastasis and migration.

The PI-3 Kinase Pathway

The PI 3-kinase pathway is characterized by a PI 3-kinase activity upon growth factor induction and a parallel signalling pathway. Growth factor stimulation of cells leads to activation of their cognate receptors at the cell membrane which in turn associate with and activate intracellular signalling molecules such as PI 3-kinase. Activation of PI 3-kinase (consisting of a regulatory p85 and a catalytic p110 subunit) results in activation of Akt by phosphorylation, thereby supporting cellular responses such as proliferation, survival or migration further downstream. PTEN is thus a tumor suppressor which is involved in the phosphatidylinositol (PI) 3-kinase pathway and which has been extensively studied in the past for its role in regulating cell growth and transformation (for reviews see, Stein, R. C. and Waterfield, M. D. (2000). PI3-kinase inhibition: a target for drug development? *Mol Med Today* 6, 347-357; Vazquez, F. and Sellers, W. R. (2000). The PTEN tumor suppressor protein: an antagonist of phosphoinositide 3-kinase signaling. *Biochim Biophys Acta* 1470, M21-35; Roymans, D. and Slegers, H. (2001). Phosphatidylinositol 3-kinases in tumor progression. *Eur J Biochem* 268, 487-498).

The tumor suppressor PTEN functions as a negative regulator of PI 3-kinase by reversing the PI 3-kinase-catalyzed reaction and thereby ensures that activation of the pathway occurs in a transient and controlled manner. Chronic hyperactivation of PI 3-kinase signalling is caused by functional inactivation of PTEN. PI 3-kinase activity can be blocked by addition of the small molecule inhibitor LY294002. The activity and downstream responses of the signalling kinase MEK which acts in a parallel pathway, can, for example, be inhibited by the small molecule inhibitor PD98059.

A chronic activation of the PI 3-kinase pathway through loss of PTEN function is a major contributor to tumorigenesis and metastasis indicating that this tumor suppressor represents an important checkpoint for a controlled cell proliferation. PTEN knock out cells show similar characteristics as cells in which the PI 3-kinase pathway has been chronically induced via activated forms of PI 3-kinase (Di Cristofano, A., Pesce, B., Cordon-Cardo, C. and Pandolfi, P. P. (1998). PTEN is essential for embryonic development and tumour suppression. *Nat Genet* 19, 348-355. Klippel, A., Escobedo, M. A., Wachowicz, M. S., Apell, G., Brown, T. W., Giedlin, M. A., Kavanaugh, W. M. and Williams, L. T. (1998). Activation of phosphatidylinositol 3-kinase is sufficient for cell cycle entry and promotes cellular changes characteristic of oncogenic transformation. *Mol Cell Biol* 18, 5699-5711. Kobayashi, M., Nagata, S., Iwasaki, T., Yanagihara, K., Saitoh, I., Karouji, Y., Ihara, S. and Fukui, Y. (1999). Dedifferentiation of adenocarcinomas by activation of phosphatidylinositol 3-kinase. *Proc Natl Acad Sci USA* 96, 4874-4879).

PTEN is involved in several pathways which are also referred to as PTEN related pathways such as the PI3K/PTEN pathway, the Akt pathway, the EGF-related autocrine loop and the mTOR pathway. A PI3-kinase pathway is actually any pathway which involves PI 3-kinase, either directly or indirectly. PI 3-kinase may act either as an inhibitor or as an activator in such pathway, or it may as such be regulated by other elements of the pathway.

Diseases and conditions involving dysregulation of the PI 3-kinase pathway are well known. Any of these conditions and diseases may thus be addressed by the inventive methods and the drugs and diagnostic agents the design, screening or manufacture thereof is taught herein. For reasons of illustration but not limitation it is referred to the following: endometrial cancer, colorectal carcinomas, gliomas, endometrial cancers, adenocarcinomas, endometrial hyperplasias, Cowden's syndrome, hereditary non-polyposis colorectal carcinoma, Li-Fraumene's syndrome, breast-ovarian cancer, prostate cancer (Ali, I. U., *Journal of the National Cancer Institute*, Vol. 92, no. 11, Jun. 7, 2000, page 861-863), Bannayan-Zonana syndrome, LDD (Lhermitte-Duklos' syndrome) (Macleod, K., supra) hamartoma-macrocephaly diseases including Cow disease (CD) and Bannayan-Ruvalcaba-Rily syndrome (BRR), mucocutaneous lesions (e.g. trichilemmonmas), macrocephaly, mental retardation, gastrointestinal harmatomas, lipomas, thyroid adenomas, fibrocystic disease of the breast, cerebellar dysplastic gangliocytoma and breast and thyroid malignancies (Vazquez, F., Sellers, W. R., supra.)

In view of this, protein kinase N beta is a valuable downstream drug target of the PI 3-kinase pathway which can be addressed by drugs which will have less side effects than other drugs directed to targets upstream of protein kinase N beta. Insofar the present invention provides a drug target which is suitable for the design, screening, development and manufacture of pharmaceutically active compounds which are more selective than those known in the art, such as, for example, LY 294002. By having control over this particular fraction of effector molecules, i.e. the protein kinase N beta and any further downstream molecule involved in the pathway, only a very limited number of parallel branches thereof or further upstream targets in the signalling cascade are likely to cause unwanted effects. Therefore, the other activities of the PI-3 kinase/PTEN pathway related to cell cycle, DNA repair, apoptosis, glucose transport, translation will not be influenced. Also, the insulin signalling is not induced which means that the diabetic responses or other side effects observed in connection with the use of LY294002 are actually avoided.

LY294002 (2-(4-morpholinyl)8-phenylchromone) is one of several chromone derivatives small molecule inhibitor developed by Lilly Research Laboratories (Indianapolis) as an inhibitor for PI-3K (Vlahos et al. 1994, *J Biol Chem.* 269, 5241-5248). It targets the catalytic subunit of the PI-3K molecule, p110 and functions by competing with ADP binding in the catalytic centre. However, LY294002 cannot distinguish between different isoforms of p110 (alpha, beta, gamma, delta) which are suggested to have different cellular functions.

Protein kinase N beta is also further downstream of mTOR which is addressed by rapamycin. mTOR (mammalian Target Of Rapamycin), also known as Raft or FRAP, is acting downstream of PI 3-kinase to regulate processes such as the pp70S6 kinase dependent entry into the cell cycle. mTOR acts as a sensor for growth factor and nutrient availability to control translation through activating pp70S6 kinase and initiation factor 4E. mTOR function is inhibited by the bacterial macrolide rapamycin which blocks growth of T-cells and certain tumor cells (Kuruvilla and Schreiber 1999, Chemistry & Biology 6, R129-R136).

The fact that rapamycin and its derivatives are suitable drugs currently being used in the clinic proves that a drug target is the more helpful and has the less side effects, the more specific it is for a particular molecular mechanism as, e.g., demonstrated by Yu et al. (Yu, K. et al (2001) Endrocrine-RelatCanc 8, 249).

Protein kinase N beta is a member of the protein kinase C family all of which are said to be protein-serine/threonine kinases. Typically, this kind of protein kinase comprises one regulatory and one catalytic subunit and uses calcium ions and phospholipids as co-factors. Diacyl glycerols act as activators of this kind of protein kinase family. Members of the protein kinase C family are involved in several signalling pathways linked to hormones or neurotransmitters. These protein kinases regulate the activity of their target proteins by phosphorylation. It is known in the art that unphysiological continued activation of protein kinase C results in the transformed cellular phenotype that might lead to the generation of cancer.

Protein Kinase N Beta and Its Derivatives

The complete sequence of protein kinase N beta as MnRNA is available in databanks, e.g., under accession numbers gi 7019488 or NM_013355. Using the genetic code, the particular amino acid sequence may be deduced from this mRNA. Also, the amino acid sequence of protein kinase N beta is available in databanks under the accession number gi 7019489 or NP_037487.1. It is within the present invention that derivatives or truncated versions thereof may be used according to the present invention as long as the desired effects may be realised. The extent of derivatization and truncation can thus be determined by one skilled in the art by routine analysis.

In the context of the present invention, the term nucleic acid sequences encoding protein kinase N beta also includes nucleic acid which hybridise to nucleic acid sequences specified by the aforementioned accession numbers or any nucleic acid sequence which may be derived from the aforementioned amino acid sequences. Such hybridization is known to the one skilled in the art. The particularities of such hybridisation may be taken from Sambrook, J. Fritsch, E. F. and Maniats, T. (1989) Molecular Cloning: A Laboratory Manual, $2^{nd}$ ed. Cold Spring Harbor: Cold Spring Harbor Laboratory. In a preferred embodiment the hybridization is a hybridization under stringent conditions, for example, under the stringent conditions specified in Sambrook supra.

In addition, a nucleic acid coding for a protein kinase N beta is also a nucleic acid sequence which contains sequence homologous to any of the aforementioned nucleic acid sequences, whereby the degree of sequence homology is preferably 75, 80, 85, 90 or 95%. Further references related to to protein kinase N beta are, among others Shibata H. et al., *J. Biochem.* (Tokyo) July 2001; 130 (1): 23-31; Dong, L Q, *Proc Natl Acad Sci USA*, 2000, May 9, 1997 (10): 5089-5094; and Oishi, K., Biochem Biophys Res Commun. 1999, Aug. 11; 261 (3): 808-814.

Homologues to human protein kinase N beta may be found, among others, in *M. musculus, R norvegicus, A. thaliana, C. elegans, D. melanogaster* and *S. cerevisiae*. The percent identity and length of the aligned region is 67% and 279 amino acids, 51% and 866 amino acids, 38% and 305 amino acids, 36% and 861 amino acids, 63% and 296 amino acids and 44% and 362 amino acids, respectively, for the various species mentioned before. It will be acknowledged by the ones skilled in the art that any of these or other homologues will in principle be suitable for the practice of the present invention provided the drug or diagnostic agent generated using such homologue may still interact with the human protein kinase N beta or any other intended protein kinase N beta.

The human amino acid sequence may also be taken from ProtEST, accession number pir: JC7083 where the respective protein kinase N beta is referred to as JC7083 protein kinase. The gene for human protein kinase N beta is located on human chromosome number 9. cDNA sources for protein kinase N beta are in general a number of cancers and various fetal or embryonic tissues, more particularly, among others, stomach, adenocarcinoma, brain, breast, Burkitt's lymphoma, cervix, chondrosarcoma, colon, fetal eyes, fetal lens, fetal eye anterior segment, fetal optic nerve, fetal retina, fetal retina foveal, fetal macular fetal choroid, fibrotheoma, germ line, nead neck, heart, kidney, large cell carcinoma, leiomyosarcoma metastatic chondrosarcoma, ovary, parathyroid, retinoblastoma, rhabdomyosarcoma, small cell carcinoma, squamous cell carcinoma, testis, and uterus.

From this list it is apparent that a drug (which is also referred to herein as a medicament), and the diagnostic agent, including a staging agent, i.e. antibody agent which can be used to differentiate the status of a patient with regard to the stage of a disease from which he might suffer, as well as for monitoring the effectiveness of a treatment applied to a patient, respectively, to be designed, screened or manufactured according to the technical teaching given herein may in addition to any of the other diseases as disclosed herein and the diseased conditions as disclosed herein also be used for the treatment, prevention, diagnosis, prognosis and monitoring of these diseases or any disease involving the specific cells, tissues or organs. These diseases and diseased conditions are also understood in the context of the invention to be included within the term "disease as described herein".

Use of Protein Kinase N Beta as a Medicament

In view of the surprising findings disclosed herein, protein kinase N beta as such may be used as a medicament for the prevention and/or treatment of the various diseases and diseased conditions as described herein, and for the manufacture of a medicament for such purpose and for the manufacture of a diagnostic agent.

When protein kinase N beta or a fragment or derivative thereof as defined above is used as a medicament itself, it is preferably used as a competitor to the naturally occurring protein kinase N beta, thereby preventing the normal biological function thereof. It is particularly preferred that the protein kinase N beta used for that purpose is catalytically defective. This kind of protein kinase N beta may either be applied to the organism and cell, respectively, or may be introduced into the organism and respective cells by means of gene therapy.

Use of Protein Kinase N Beta as a Target

Apart from being a potential drug itself, protein kinase N beta may be used as a target against which chemical compounds which may be used as drugs or drug candidates or as diagnostic agents, are directed. Suitable chemical compounds belonging to different classes of compounds such as antibodies, peptides, anticalines, aptamers, spiegelmers, ribozymes, antisense oligonucleotides and siRNA as well as small molecules may be used. The compounds are designed, selected, screened generated and/or manufactured by either using protein kinase N beta itself as a physical or chemical entity, or information related to protein kinase N beta.

In the design, selection, screening, generation and/or manufacturing process of said classes of compounds protein kinase N beta will also be referred to as the target which is used in the process rather than in the final application of the respective compound to a patient in need thereof. In the processes which provide the various classes of compounds, either the protein protein kinase N beta, also referred to herein as protein kinase N beta or a nucleic acid coding for protein kinase N beta may be used. The term protein kinase N beta as used herein comprises any fragment or derivative of protein kinase N beta which allows the design, selection, screening, generation and/or manufacture of said classes of compounds of the respective class(es) of compounds which in turn are/is upon their/its application as a medicament or as a diagnostic agent active as such.

The term nucleic acid coding for protein kinase N beta as used herein shall comprise any nucleic acid which contains a nucleic acid which codes for protein kinase N beta as defined above, or a part thereof. A part of a nucleic acid coding for protein kinase N beta is regarded as such as long as it is still suitable for the design, selection, screening, generation and/or manufacture of said classes of compounds which in turn are/is upon their/its application as a medicament or as a diagnostic agent active as such. The nucleic acid coding for protein kinase beta N may be genomic nucleic acid, hnRNA, mRNA, cDNA or part of each thereof.

As outlined above it is within the present invention that apart from protein kinase N beta or a part or derivative thereof or a nucleic acid sequence therefore, as described herein, also other means or compounds may be used in order to create or to suppress the effects arising from protein kinase N beta or the nucleic acid coding protein kinase N beta. Such means may be determined or selected in a screening method. In such screening method a first step is to provide one or several so called candidate compounds. Candidate compounds as used herein are compounds the suitability of which is to be tested in a test system for treating or alleviating the various diseases as described herein and diseased conditions as described herein or to be used as a diagnostic means or agent for this kind of diseases and diseased conditions.

If a candidate compound shows a respective effect in a test system said candidate compound is a suitable means or agent for the treatment of said diseases and diseased conditions and, in principle, as well a suitable diagnostic agent for said diseases and diseased conditions. In a second step the candidate compound is contacted with a protein kinase N beta expression system or a protein kinase N beta gene product, preferably a respective gene expression product, such as a hnRNA or MRNA, or a protein kinase N beta activity system or a protein kinase N beta. The protein kinase N beta activity system is also referred to herein as and/or is preferably also active in the meaning of a system detecting the activity of protein kinase N beta.

The protein kinase N beta screening methodology described herein also is useful to eliminate non-functional or inactive compounds from further consideration. Thus protein kinase N beta activity can be measured in a first sample obtained from a subject or test system, generating a pre-treatment level, followed by administering a test agent to the subject or test system and measuring protein kinase N beta activity in a second sample from the subject or test system at a time following administration of the test agent, thereby generating data for a test level. The pre-treatment level can be compared to the test level, and data showing no decrease in the test level relative to the pre-treatment level indicates that the test agent is not effective in the subject, and the test agent may be eliminated from further evaluation or study. Conversely, a change in values can indicate that the test agent is suitable for use as a PKN beta inhibitor or for further study.

A protein kinase N beta expression system as that term is used herein is basically an expression system that shows or displays the expression of protein kinase N beta, whereby the extent or level of expression may be changed. Preferably, a protein kinase N beta activity system is essentially an expression system whereby the activity or condition of activity is measured rather than the expression of protein kinase N beta. Alternatively, a protein kinase activity system is a protein kinase N beta the activity of which can be measured, or a system providing or comprising protein kinase N beta.

Detection and Inhibition of Protein Kinase N Beta Activity

In any of these systems it is determined whether under the influence of a candidate compound the activity of protein kinase N beta or of the nucleic acid coding protein kinase N beta is different from the situation without the candidate compound. Regardless whether the particular system is either an expression system or an activity system, it is within the scope of the present invention that either an increase or a decrease of the activity and expression, respectively, may occur and be measured. Typically, the expression system and/or activity system is an in vitro reaction, such as a cell extract or a fraction of the cell extract such as a nuclear extract. A protein kinase N beta expression system as used herein may also be a cell, preferably a cell of a tissue or organ involved in the diseases as described herein and diseased conditions as described herein.

Whether there is an increase or decrease in the activity system or expression system may be determined at each level of the expression, for example by measuring the increase or decrease of the amount of nucleic acid coding for protein kinase N beta, more particularly mRNA, or the increase or decrease of protein kinase N beta polypeptide expressed under the influence of the candidate compound. The techniques required for such measurements, more particularly the quantitative measurement of these kinds of changes, such as for the MRNA or the protein are known to the one skilled in the art. Also known to the one skilled in the art are methods to determine the amount of or content of protein kinase N beta, e.g. by detection using appropriate antibodies. Antibodies may be generated as known to the one skilled in the art and described, e.g. by Harlow, E., and Lane, D., "Antibodies: A Laboratory Manual," Cold Spring Harbor Laboratory, Cold Spring Harbor, N.Y.,(1988). Suitable antibodies may also be generated by other well known methods, for example, by phage display selection from libraries of antibodies.

In case of a protein kinase N beta expression system an increase or decrease of the activity of protein kinase N beta may be determined, preferably in a functional assay.

Contacting the candidate compound and the expression system and activity system, respectively, usually is performed by adding an aqueous solution of the candidate compound to a respective reaction system which is generally referred to herein as the test system. Besides aqueous solutions, suspensions or solutions of the candidate compound in organic solvents or in mixtures of organic and aqueous solvents may be used. The aqueous solution is preferably a buffer solution.

Preferably, in each run using the expression system and activity system, respectively, only a single candidate compound is used. However, it is also within the present invention that several of this kind of tests are performed in parallel in a high throughput system using methods known in the art.

A further step in the method according to the present invention resides in determining whether under the influence of the candidate compound the expression or activity of the expression system and activity system, respectively, in relation to protein kinase N beta or a nucleic acid coding therefore is changed. Typically this is done by comparing the system's reaction upon addition of the candidate compound relative to the one without addition of the candidate compound. Preferably, the candidate compound is a member of a library of compounds.

Basically any library of compounds is suitable for the purpose of this invention regardless of the class of compounds. Suitable libraries of compounds are, among others, libraries composed of small molecules, of peptides, proteins, antibodies, anticalines and functional nucleic acids. The latter compounds may be generated as known to the one skilled in the art and outlined herein.

Antibodies

The manufacture of an antibody specific for the protein of protein kinase N beta or for the nucleic acid coding for protein kinase N beta, is known to the one skilled in the art and, for example, described in Harlow, E., and Lane, D., "Antibodies: A Laboratory Manual," Cold Spring Harbor Laboratory, Cold Spring Harbor, N.Y.,(1988). Monoclonal antibodies may be used in connection with the present invention which may be manufactured according to the protocol of Cesar and Milstein and further developments based thereon, for example by selection from antibody libraries by, for example, phage display. See for example, U.S. Pat. No. 5,969,108, the disclosure of which is hereby incorporated by reference in its entirety. Antibodies as used herein, include, but are not limited to, complete antibodies, antibody fragments or derivatives such as Fab fragments, Fc fragments and single-stranded antibodies, as long as they are suitable and capable of binding to protein kinase N beta. Apart from monoclonal antibodies also polyclonal antibodies may be used and/or generated. The generation of polyclonal antibodies is also known to the one skilled in the art and, for example, described in Harlow and Lane supra. Preferably, the antibodies used for therapeutic purposes are humanized or human antibodies as defined above.

The antibodies which may be used according to the present invention may have one or several markers or labels. Such markers or labels may be useful to detect the antibody either in its diagnostic application or its therapeutic application. Preferably the markers and labels are selected from the group comprising avidine, streptavidine, biotin, gold and fluorescein and used, e.g., in ELISA methods. These and further markers as well as methods are, e.g. described in Harlow and Lane, supra.

It is also within the present invention that the label or marker exhibits an additional function apart from detection, such as interaction with other molecules. Such interaction may be, e.g., specific interaction with other compounds. These other compounds may either be those inherent to the system where the antibody is used such as the human or animal body or the sample which is analysed by using the respective antibody. Appropriate markers may, for example, be biotin or fluorescein with the specific interaction partners thereof such as avidin and streptavidin and the like being present on the respective compound or structure to interact with the thus marked or labelled antibody.

Peptides

A further class of medicaments as well as diagnostic agents which may be generated using the protein of protein kinase N beta or the nucleic acid coding for protein kinase beta, are peptides which bind thereto. Such peptides may be generated by using methods according to the state of the art such as phage display. Basically, a library of peptides is generated and displayed on the surface of phage, and the displayed library is contacted with the target molecule, in the present case, for example, the protein kinase N beta. Those peptides binding to the target molecule are subsequently removed, preferably as a complex with the target molecule, from the respective reaction. It is known to the one skilled in the art that the binding characteristics, at least to a certain extend, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterized.

Prior to the characterisation optionally an amplification step is realized such as, e.g. by propagating the peptide coding phages. The characterization preferably comprises the sequencing of the target binding peptides. Basically, the peptides are not limited in their lengths, however, preferably peptides having a lengths from about 8 to 20 amino acids are preferably obtained in the respective methods. The size of the libraries may be about $10^2$ to $10^{18}$, preferably $10^8$ to $10^{15}$ different peptides, however, is not limited thereto.

Anticalines

A particular form of target binding polypeptides are the so-called "anticalines" which are, among others, described in German patent application DE 197 42 706, the disclosure of which is hereby incorporated by reference.

According to the present invention the protein of protein kinase N beta as well as the nucleic acid coding for protein kinase N beta may be used as the target for the manufacture or development of a medicament for the treatment of the diseases described herein and of the diseased conditions described herein, as well as for the manufacture and/or development of means for the diagnosis of said diseases and said conditions, in a screening process, whereby in the screening process small molecules or libraries of small molecules are used. This screening comprises the step of contacting the target molecule with a single small molecule or a variety (such as a library) of small molecules at the same time or subsequently, preferably those from the library as specified above, and identifying those small molecules or members of the library which bind to the target molecules which, if screened in connection with other small molecules may be separated from the non-binding or non-interacting small molecules.

The binding and non-binding may strongly be influenced by the particular experimental set-up. In modifying the stringency of the reaction parameters it is possible to vary the degree of binding and non-binding which allows a fine tuning of this screening process. Preferably, after the identification of one or several small molecules which specifically interact with the target molecule, this small molecule may be further characterized. This further characterisation may, for example, reside in the identification of the small molecule and determination of its molecule structure and further physical, chemical, biological and/or medical characteristics. Preferably, the natural compounds have a molecular weight of about 100 to 1000 Da. Also preferably, small molecules are those which comply with the Lepinsky rules of five known to the ones skilled in the art. Alternatively, small molecules may also be defined such that they are synthetic-small-molecules, preferably arising from combinatorial chemistry, in contrast to natural products which preferably are non-synthetic. However, it is to be noted that these definitions are only subsidiary to the general understanding of the respective terms in the art. Like all kinases, protein kinase N beta contains an ATP-binding site and drugs that are known to bind to such sites are therefore suitable candidate compounds for inhibiting protein kinase N beta. Examples if suitable compounds include, but are not limited to, Y-27632, Ro-3 1-8220, and HA 1077, all of which are available from Calbiochem (La Jolla, Calif.).

Aptamers and Speigelmers

It is also within the present invention to use the protein kinase N beta and/or a nucleic acid coding for protein kinase N beta as a target molecule for the manufacture or selection of aptamers and spiegelmers which may then be used directly or indirectly either as medicament or as diagnostic agents.

Aptamers are D-nucleic acids which are either single stranded or double stranded and which specifically interact with a target molecule. The manufacture or selection of aptamers is, e.g., described in European patent EPO 533 838, the specification of which is hereby incorporated by reference in its entirety. Basically the following steps are realized. First, a mixture of nucleic acids, i.e. potential aptamers, is provided whereby each nucleic acid typically comprises a segment of several, preferably at least eight, subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the nucleic acid(s) thus obtained is amplified using, e.g. a polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to aptamers.

It is apparent that at any stage of the method for the generation or identification of the aptamers samples of the mixture of individual nucleic acids may be taken to determine the sequence thereof using standard techniques. It is within the present invention that the aptamers may be stabilized -such as, e.g., by introducing defined chemical groups which are known to the one skilled in the art of generating aptamers. Such modification may for example reside in the introduction of an amino group at the 2'-position of the sugar moiety of the nucleotides. Aptamers are currently used as therapeutical agents.

However, it is also within the present invention that the thus selected or generated aptamers may be used for target validation and/or as lead substance for the development of medicaments, preferably of medicaments based on small molecules. This is actually done by a competition assay whereby the specific interaction between the target molecule and the aptamer is inhibited by a candidate drug whereby upon replacement of the aptamer from the complex of target and aptamer it may be assumed that the respective drug candidate allows a specific inhibition of the interaction between target and aptamer, and if the interaction is specific, said candidate drug will, at least in principle, be suitable to block the target and thus decrease its biological availability or activity in a respective system comprising such target. The small molecule thus obtained may then be subject to further derivatisation and modification to optimise its physical, chemical, biological and/or medical characteristics such as toxicity, specificity, biodegradability and bioavailability.

The generation or manufacture of spiegelmers which may be used or generated according to the present invention using protein kinase N beta or a nucleic acid coding for protein kinase N beta, is based on a similar principle. The manufacture of spiegelmers is described in the international patent application WO 98/08856. Spiegelmers are L-nucleic acids, which means that they are composed of L-nucleotides rather than aptamers which are composed of D-nucleotides as aptamers are. Spiegelmers are characterized by the fact that they have a very high stability in biological system and, comparable to aptamers, specifically interact with the target molecule against which they are directed. In the purpose of generating spiegelmers, a heterogonous population of D-nucleic acids is created and this population is contacted with the optical antipode of the target molecule, in the present case for example with the D-enantiomer of the naturally occurring L-enantiomer of the protein kinase N beta. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

Ribozymes, Antisense Oligonucleotides and siRNA.

A further class of compounds which may be manufactured or generating based on protein kinase N beta or a nucleic acid coding for protein kinase beta, as the target molecule as disclosed herein, are ribozymes, antisense oligonucleotides and siRNA.

It is a common feature of all of the aforementioned nucleic acids that they do not interact with the target molecule at the level of the translation product which is in the present case the protein kinase N beta, but rather interact with the transcription product, i.e. the nucleic acid coding for protein kinase beta such as the genomic nucleic acid or any nucleic acid derived therefrom such as the corresponding hnRNA, cDNA and MRNA, respectively. Insofar, the target molecule of the aforementioned class of compounds is preferably the mRNA of protein kinase N beta.

Ribozymes

Ribozymes are catalytically active nucleic acids which preferably consist of RNA which basically comprises two moieties. The first moiety shows a catalytic activity whereas the second moiety is responsible for the specific interaction with the target nucleic acid, in the present case the nucleic acid coding for protein kinase N beta. Upon interaction between the target nucleic acid and the second moiety of the ribozyme, typically by hybridisation and Watson-Crick base pairing of essentially complementary stretches of bases on the two hybridising strands, the catalytically active moiety may become active which means that it catalyses, either intramolecularly or intermolecularly, the target nucleic acid in case the catalytic activity of the ribozyme is a phosphodiesterase activity. Subsequently, there may be a further degradation of the target nucleic acid which in the end results in the degradation of the target nucleic acid as well as the protein derived from the said target nucleic acid which in the present case is protein kinase N beta due to a lack of newly synthesized protein kinase N beta and a turn-over of prior existing protein kinase N beta. Ribozymes, their use and design principles are known to the one skilled in the art, and, for example described in Doherty and Doudna (Ribozyme structures and mechanism. *Annu Rev. Biophys. Biomolstruct.* 2001; 30:457- 75) and Lewin and Hauswirth (Ribozyme Gene Therapy: Applications for molecular medicine. 20017: 221-8).

Antisense Oligonucleotides

The use of antisense oligonucleotides for the manufacture of a medicament and as a diagnostic agent, respectively, is based on a similar mode of action. Basically, antisense oligonucleotides hybridise based on base complementarity, with a target RNA, preferably with a mRNA, thereby activating RNase H. RNase H is activated by both phosphodiester and phosphorothioate-coupled DNA. Phosphodiester-coupled DNA, however, is rapidly degraded by cellular nucleases but phosphorothioate-coupled DNA is more stable. These resistant, non-naturally occurring DNA derivatives do not inhibit RNase H upon hybridisation with RNA. In other words, antisense polynucleotides are only effective as DNA RNA hybrids complexes. Examples for this kind of antisense oligonucleotides are described, among others, in U.S. Pat. Nos. 5,849,902 and 5,989,912. In other words, based on the nucleic acid sequence of the target molecule which in the present case is the nucleic acid coding for protein kinase N beta, either from the target protein from which a respective nucleic acid sequence may in principle be deduced, or by knowing the nucleic acid sequence as such, particularly the mRNA, suitable antisense oligonucleotides may be designed base on the principle of base complementarity.

Particularly preferred are antisense-oligonucleotides which have a short stretch of phosphorothioate DNA (3 to 9 bases). A minimum of 3 DNA bases is required for activation of bacterial RNase H and a minimum of 5 bases is required for mammalian RNase H activation. In these chimeric oligonucleotides there is a central region that forms a substrate for RNase H that is flanked by hybridising "arms" comprised of modified nucleotides that do not form substrates for RNase H. The hybridising arms of the chimeric oligonucleotides may be modified such as by 2'-O-methyl or 2'-fluoro. Alternative approaches used methylphosphonate or phosphoramidate linkages in said arms. Further embodiments of the antisense oligonucleotide useful in the practice of the present invention are P-methoxyoligonucleotides, partial P-methoxyoligodeoxyribonucleotides or P-methoxyoligonucleotides.

Of particular relevance and usefulness for the present invention are those antisense oligonucleotides as more particularly described in the above two mentioned U.S. patents. These oligonucleotides contain no naturally occurring 5'→3'-linked nucleotides. Rather the oligonucleotides have two types of nucleotides: 2'-deoxyphosphorothioate, which activate RNase H, and 2'-modified nucleotides, which do not. The linkages between the 2'-modified nucleotides can be phosphodiesters, phosphorothioate or P-ethoxyphosphodiester. Activation of RNase H is accomplished by a contiguous RNase H-activating region, which contains between 3 and 5 2'-deoxyphosphorothioate nucleotides to activate bacterial RNase H and between 5 and 10 2'-deoxyphosphorothioate nucleotides to activate eucaryotic and, particularly, mammalian RNase H. Protection from degradation is accomplished by making the 5' and 3' terminal bases highly nuclease resistant and, optionally, by placing a 3' terminal blocking group.

More particularly, the antisense oligonucleotide comprises a 5' terminus and a 3' terminus; and from 11 to 59 5'→3'-linked nucleotides independently selected from the group consisting of 2'-modified phosphodiester nucleotides and 2'-modified P-alkyloxyphosphotriester nucleotides; and wherein the 5'-terminal nucleoside is attached to an RNase H-activating region of between three and ten contiguous phosphorothioate-linked deoxyribonucleotides, and wherein the 3'-terminus of said oligonucleotide is selected from the group consisting of an inverted deoxyribonucleotide, a contiguous stretch of one to three phosphorothioate 2'-modified ribonucleotides, a biotin group and a P-alkyloxyphosphotriester nucleotide.

Also an antisense oligonucleotide may be used wherein not the 5' terminal nucleoside is attached to an RNase H-activating region but the 3' terminal nucleoside as specified above. Also, the 5' terminus is selected from the particular group rather than the 3' terminus of said oligonucleotide.

Suitable and useful antisense oligonucleotides are also those comprising a 5' terminal RNase H activating region and having between 5 and 10 contiguous deoxyphosphorothioate nucleotides; between 11 to 59 contiguous 5'→3'-linked 2'-methoxyribonucleotides; and an exonuclease blocking group present at the 3' end of the oligonucleotide that is drawn from the group consisting of a non-5 '-3'-phosphodiester-linked nucleotide, from one to three contiguous 5'-3'-linked modified nucleotides and a non-nucleotide chemical blocking group.

Two classes of particularly preferred antisense oligonucleotides can be characterized as follows:

The first class of antisense oligonucleotides, also referred to herein as second generation of antisense oligonucleotides, comprises a total of 23 nucleotides comprising in 5'→3' direction a stretch of seven 2'-O-methylribonucleotides, a stretch of nine 2'-deoxyribonucleotides, a stretch of six 2'-O-methylribonucleotides and a 3'-terminal 2'-deoxyribonucleotide. From the first group of seven 2'-O-methylribonucleotides the first four are phosphorothioate linked, whereas the subsequent four 2'-O-methylribonucleotides are phosphodiester linked. Also, there is a phosphodiester linkage between the last, i.e. the most 3'-terminal end of the 2'-O-methylribonucleotides and the first nucleotide of the stretch consisting of nine 2'-deoxyribonucleotides. All of the 2'-deoxyribonucleotides are phosphorothioate linked. A phosphorothioate linkage is also present between the last, i.e. the most 3'-terminal 2'-deoxynucleotide, and the first 2'-O-methylribonucleotide of the subsequent stretch consisting of six 2'-O-methylribonucleotides. From this group of six 2'-O-methylribonucleotides the first four of them, again in 5'→3' direction, are phosphodiester linked, whereas the last three of them, corresponding to positions 20 to 22 are phosphorothioate linked. The last, i.e. terminal 3'-terminal 2'-deoxynucleotide is linked to the last, i.e. most 3'-terminal 2'-O-methylribonucleotide through a phosphorothioate linkage.

This first class may also be described by reference to the following schematic structure: RRRnnnnNNNNNNNNNnnnRRRN. Hereby, R indicates phosphorothioate linked 2'-O-methyl ribonucleotides (A, G, U, C); n stands for 2'-O-methyl ribonucleotides (A, G, U, C); N represents phosphorothioate linked deoxyribonucleotides (A, G, T, C).

The second class of particularly preferred antisense oligonucleotides, also referred to herein as third generation (of) antisense oligonucleotides or GeneBlocs, also comprises a total of 17 to 23 nucleotides with the following basic structure (in 5'→3' direction).

At the 5'-terminal end there is an inverted abasic nucleotide which is a structure suitable to confer resistance against exonuclease activity and, e.g., described in WO 99/54459. This inverted abasic is linked to a stretch of five to seven 2'-O-methylribonucleotides which are phosphodiester linked. Following this stretch of five to seven 2'-O-methylribonucleotides there is a stretch of seven to nine 2'-deoxyribonucleotides all of which are phosphorothioate linked. The linkage between the last, i.e. the most 3'-terminal 2'-O-methylribonucleotide and the first 2'-deoxynucleotide of the 2'-deoxynucleotide comprising stretch occurs via a phosphodiester linkage. Adjacent to the stretch of seven to nine 2'-deoxynucleotides a stretch consistent of five to seven 2'-O-methylribonucleotides S is connected. The last 2'-deoxynucleotide is linked to the first 2'-O-methylribonucleotide of the latter mentioned stretch consisting of five to seven 2'-O-methylribonucleotides occurs via a phosphorothioate linkage. The stretch of five to seven 2'-O-methylribonucleotides are phosphodiester linked. At the 3'-terminal end of the second stretch of five to seven 2'-O-methylribonucleotide another inverted abasic is attached.

This second class may also be described by reference to the following schematic structure: (GeneBlocs representing the 3rd generation of antisense oligonucleotides have also the following schematic structure:) cap-$(n_p)_x(N_s)_y(n_p)_z$-cap or cap-nnnnnnnNNNNNNNNnnnnnnn-cap. Hereby, cap represents inverted deoxy abasics or similar modifications at both ends; n stands for 2'-O-methyl ribonucleotides (A, G, U, C); N represents phosphorothioate-linked deoxyribonucleotides (A, G, T, C); x represents an integer from 5 to 7; y represents an integer from 7 to 9; and z represents an integer from 5 to 7.

It is to be noted that the integers x, y and z may be chosen independently from each other although it is preferred that x and z are the same in a given antisense oligonucleotide. Accordingly, the following basic designs or structures of the antisense oligonucleotides of the third generation can be as follows: cap-$(n_p)_5(N_s)_7(n_p)_5$-cap, cap-$(n_p)_6(N_s)_7(n_p)_5$-cap, cap-$(n_p)_7(N_s)_7(n_p)_5$-cap, cap-$(n_p)_5(N_s)_8(n_p)_5$-cap, cap-$(n_p)_6(N_s)_8(n_p)_5$-cap, cap-$(n_p)_7(N_s)_8(n_p)_5$-cap, cap-$(n_p)_5(N_s)_9(n_p)_5$-cap, cap-$(n_p)_6(NS)_9(n_p)$S-cap, cap-$(n_p)_7(NS)g(n_p)_5$-cap, cap-$(n_p)_5(NS)_7(n_p)_6$-cap, cap-$(n_p)_6(N_s)_7(n_p)_6$-cap, cap-$(n_p)_7(N_s)_7(n_p)_6$-cap, cap-$(n_p)_5(N_s)_8(n_p)_6$-cap, cap-$(n_p)_6(N_s)_8(n_p)_6$-cap, cap-$(n_p)_7(N_s)_8(n_p)_6$-cap, cap-$(n_p)_5(N_s)_9(n_p)_6$-cap, cap-$(n_p)_6(N_s)_9(n_p)_6$-cap, cap-$(n_p)_7(N_s)_9(n_p)_6$-cap, cap-$(n_p)_5(N_s)_7(n_p)_7$-cap, cap-$(n_p)_6(N_s)_7(n_p)_7$-cap, cap-$(n_p)_7(N_s)_7(n_p)_7$cap, cap-$(n_p)_5(NS)s(n_p)_7$-cap, cap-$(n_p)_6(N_s)_8(n_p)_7$-cap, cap-$(n_p)_7(N_s)g(n_p)_7$-cap, cap-$(n_p)_5(N_s)_9(n_p)_7$-cap, cap-$(n_p)_6(N_5)_9(n_p)_7$-cap and cap-$(n_p)_7(NS)_9(n_p)_7$-cap.

siRNA Molecules and RNAi

A further class of compounds which may be generated based on the technical teaching given herein and which may be used as medicaments and/or diagnostic agents are small interfering RNA (siRNA) directed to the nucleic acid, preferably MRNA, coding for protein kinase N beta. siRNA is a double stranded RNA having typically a length of about 21 to about 23 nucleotides. The sequence of one of the two RNA strands corresponds to the sequence of the target nucleic acid such as the nucleic acid coding for protein kinase N beta, to be degraded. In other words, knowing the nucleic acid sequence of the target molecule, in the present case protein kinase N beta, preferably the MRNA sequence, a double stranded RNA may be designed with one of the two strands being complementary to said, e.g. MRNA of protein kinase N beta and, upon application of said siRNA to a system containing the gene, genomic DNA, hnRNA or MRNA coding for protein kinase N beta, the respective target nucleic acid will be degraded and thus the level of the respective protein be reduced. The basic principles of designing, constructing and using said siRNA as medicament and diagnostic agent, respectively, is, among others, described in international patent applications WO 00/44895 and WO 01/75164.

Based on the aforementioned design principles, it is possible to generate such siRNA, antisense oligonucleotide and ribozyme, respectively, once the nucleic acid sequence coding for protein kinase N beta is known. This is also true for precursor molecules of nucleic acid such as hnRNA, cDNA and the like, including genomic nucleic acid. Of course, also knowing the respective antisense strand may allow the design of such nucleic acid based compounds given the basic principle of base pair complementarity, preferably based on Watson-Crick base pairing. Accordingly, a further aspect of the present invention is related to specific siRNAs, ribozymes and antisense nucleotides which are directed against or specific for protein kinase N-beta. In the following, this is further illustrated by siRNA, however, this applies to antisense oligonucleotides and ribozymes as well, as will be acknowledged by the ones skilled in the art.

Such siRNA comprises preferably a length of from 15 to 25 nucleotides, whereby this means actually any length comprising 15, 16, 17, 18, 20, 21, 22, 23, 24 or 25 nucleotides. In further embodiments, the siRNA may even exhibit more nucleotides. According the design principles well known in the art, respective siRNA can be generated. Accordingly, the siRNA claimed herein comprises a stretch of preferably any nucleotide length from 15 to 25 consecutive nucleotides which is either at least partially complementary to the sense or to the antisense strand encoding PKN-beta, and a second ribonucleotide strand which is at least partially complementary to the first one and thus to the antisense strand and sense strand respectively, encoding protein kinase N-beta. Any design principle known in the art of generation or manufacture of siRNA may be applied to this kind of duplex structure. The siRNA space disclosed herein comprises siRNA molecules the antisense strand of which starts with a nucleotides which corresponds to nucleotide no. 1 of a PKN-beta encoding sequence as specified above. Further such siRNA molecules start with a nucleotide which corresponds to-nucleotide no 2 of a PKN-beta encoding sequence as specified above, and so on. This kind of scanning over the PKN-beta encoding sequence is repeated so as to provide all possible siRNA molecules which can be directed against PKN-beta. The length of any of the siRNA molecules thus generated may be any length suitable for siRNA, more particularly any length as specified above. Preferably, the various siRNA molecule of the siRNA molecule space disclosed herein, overlap except the most 5'terminal nucleotide of the antisense strand or sense strand. It is obvious that the thus obtained antisense sequences have to complemented through base pairing so as to form the at least partially double-stranded structure required for a functionally active siRNA Pharmaceutical and Diagnostic Compositions Based on the mode of action of the aforementioned classes of compounds, such as antibodies, peptides, anticalines, aptamers, spiegelmers, ribozymes, antisense oligonucleotides as well as siRNA, it is thus also within the present invention to use any of these compounds targeting protein kinase N beta and the nucleic acid coding therefore, respectively, for the manufacture of a medicament or a diagnostic agent for any of the diseases as described herein and any of the diseased conditions described herein. Furthermore, these agents may be used to monitor the progression of said diseases and diseased conditions and the success of any therapy applied, respectively.

The various classes of compounds designed according to the present invention such as antibodies, peptides, anticalines, small molecules, aptamers, spiegelmers, ribozymes, antisense oligonucleotides and siRNA may also be contained in a pharmaceutical composition. Preferably such pharmaceutical composition is used for the treatment of the diseases as described herein or the diseased conditions described herein. The pharmaceutical composition may comprise in an embodiment one or several of the aforementioned classes of compounds and/or one or more members of a single class, and optionally a further pharmaceutical active compound, and a pharmaceutically acceptable carrier. Such carrier may be either liquid or solid, for example a solution, a buffer, an alcoholic solution or the like. Suitable solid carriers are, among others, starch and the like. It is known to the one skilled in the art to provide respective formulations for the various compounds according to the aforementioned classes of compounds in order to realize the particular route of administrations such as oral, parenteral, subcutaneous, intravenous, intramuscular and the like.

The various compounds of the different classes of compounds as mentioned above, may also be, either alone or in combination, subject to or contained in a kit. Such kit comprises apart from the respective compound(s) additionally one or several further elements or compounds whereby the elements are selected from the group comprising buffers, negative controls, positive controls and instructions on the use of the various compounds. Preferably, the various compounds are present in either dry or liquid form, preferably as a unit dosage for a single administration each. The kit may particularly be used for the therapy, diagnosis or monitoring of the progress of the disease or applied therapies in relation to the diseases and diseased conditions as described herein.

The invention is further exemplified by the following examples, which are not limiting of the scope of the invention.

EXAMPLE 1

Materials and Methods

Cell Culture

Human prostate carcinoma PC-3 cells were obtained from the American Type Culture Collection (ATCC). Cells were cultured in FI2K Nutrient Mixture (Kaighn's modification) containing, 10% fetal calf serum (CS), gentamycin (50 µg/ml) and amphotericin (50 ng/ml).

Transfections were carried out in 96 well or 10-cm plates (at 30% to 50% confluency) by using various cationic lipids such as Oligofectamine, Lipofectamine (Life Technologies), Argfectin50 or Profectin50 (Atugen/GOT Berlin, Germany), or FuGene 6 (Roche) according to the manufacturer's instructions. GeneBlocs were transfected by adding pre-formed 5× concentrated complex of GeneBloc and lipid in serum-free medium to cells in complete medium. The total transfection volume was 100 µl for cells plated in 96 wells and 10 ml for cells in 10 cm plates. The final lipid concentration was 0.8 to 1.2 µg/ml depending on cell density; the GeneBloc concentration is indicated in each experiment.

Cultivated cells were trypsinized and harvested following stopping the trypsin effect by medium. The cells were washed (PBS; Centrifugation 5 min/1.000 rpm) and, finally, the pellet was resuspended at a concentration that depended on the cell number and volume to be inoculated.

Determination of the Relative Amounts of RNA Levels by Taqman Analysis.

RNA from cells transfected in 96-wells was isolated and purified using the Invisorb RNA HTS 96 kit (InVitek GmbH, Berlin). Inhibition of PKN beta mRNA expression was detected by real time RT-PCR (Taqman) analysis using 300 nM PKNbeta 5' primer, 300 nM PKNbeta 3' primer and 100 nM of the PKNbeta Taqman probe Fam-Tainra labelled. The reaction was carried out in 50 gl and assayed on the ABI PRISM 7700 Sequence detector (Applied Biosystems) according to the manufacturer's instructions under the following conditions: 48° C. for 30 min, 95° C. for 10 min, followed by 40 cycles of 15 sec at 95° C. and 1 min at 60° C.

In Vitro Growth on Matrigel Matrix.

PC3 cells were tretated with 5 μM LY294002 or DMSO when seeded on Matrigel. If cells were trnasfected previous to seeding cells were transfected with GeneBloc and trypsinized 48 h post transfection. The cells were washed in medium and seeded into duplicate 24-wells (100.000 cells per well) precoated with 250 μl matrigel basement membrane matrix (Becton Dickinson). After incubation for 24 to 72 h photographs were taken at 5× magnification with an Axiocam camera attached to an Axiovert S100 microscope (Zeiss).

Affymetrix

Total RNA from cells grown on Matrigel was prepared using Totally RNA kit (AMBION) following manufacturers protocol. In the final step precipitated total RNA was resuspended in Invisorb lysis buffer and purified using the Invisorb spin cell-RNA kit (INVITEK). Biotin-labeled cRNA was prepared following Affymetrix protocols and 15 μg cRNA were hybridized onto Affymetrix GeneChip set HG-U95.

Data Analysis

Raw data were analyzed using Affymetrix GeneChip software Microarray Suite v4.0. The intensity of each probe set is calculated as difference of the hybridization signal of perfect match oligonucleotides compared to mismatch oligonucleotides averaged over the set of 16 to 20 probe pairs corresponding to one transcript. The average difference of a probe set is proportional to the abundance of a transcript. Total signal intensities of different arrays were scaled to the same value before comparison. Fold changes were calculated using the Affymetrix software by pairwise comparison of the intensities of corresponding probe pairs from experiment and baseline arrays. Using decision matrices described by Affymetrix the software also generates absolute calls (transcript is absent, marginal or present in an experiment) and difference calls (abundance of a transcript in one experiment compared to another: increase, marginal increase, no change, marginal decrease, decrease). Results were exported to Microsoft Excel (absolute call, difference call, fold change) and filtered. All probe sets with absent calls or a no change call were discarded and the table sorted by the fold change.

Animal Studies

The in vivo experiments were conducted corresponding the Good Laboratory Practice for Nonclinical Laboratory Studies (GLP Regulations) of the Food and Drug Administration and in accordance with the German animal protection law as legal basis.

Male Shoe:NMRI-nu/nu mice (Tierzucht Sch6nwalde GmbH) maintained under SPF conditions (Laminar air flow equipment, Scantainer, Scanbur) served as recipients for the human prostate carcinoma cells. The animals, aged 6-8 weeks and weighing 28-30 g, were inoculated $2\times10^6/0,03$ ml tumor cells into both, the left dorsolateral lobe of the prostatic gland (iprost; Orthotopic) or the tip of the Lobus lateralis sinister of the liver (ihep; Ectopic). For this purpose, the mice received a total body anaesthesia using a mixture of Ketanest (Parke-Davis GmbH) and Rompun (Bayer Vital GmbH) 80:1 with dosages of 100 mg/kg and 5 mg/kg, respectively. Following the thorough sterilization of the ventral body surface an incision was carried out through the abdominal skin and peritoneal wall beginning near the border of the preputial gland and measuring about 1 cm. By means of a pair of tweezers and a cotton swab the prostatic gland was visualized. The orthotopic cell challenges followed with the help of a magnifying glas and by usage of a 1 ml syringe (Henke Sass Wolf GmbH) bearing 30G 0,30×13 microlance needles (Becton Dickinson). An administration was successful observing a marked bleb at the inoculation site. The wound was closed by suture material (PGA Resorba, Franz Hiltner GmbH) concerning the peritoneal wall and Michel clamps 11×2 mm (Heiland) for the abdominal skin. Wound spray (Hansaplast Spruhpflaster, Beiersdorf AG) covered the lesion. During the postsurgical phase the animals were maintained in a warmed environment until the complete waking up. The animals were randomised according to the number of treatment groups consisting of 5-10 animals per group each. They were inspected successively inclusive of protocolling the findings. Ssniff NM-Z, 10 mm, autoclavable (ssniff Spezialdiaten GmbH) is administered as fortified diet and drinking water is acidified by HCl, both ad libitum.

Evaluations

To receive the actual dosage level body weights were registered on the treatment days. At the same time, it can be derived from body weight development to recognize influences of treatment modalities on the whole organism.

Blood punctures were carried out on day 0 (Base line); 14; 28; and 35 (Sacrificing). Blood was drawn from the orbital vein of the short term anaesthesized animal (Diethylether, Otto Fischar GmbH). Evaluation parameters giving data to the compatibility and side effects of the treatments are the following: Leukocyte numbers; Thrombocyte numbers; Enzymes. Further blood borne parameters were bilirubin; creatinine; protein; urea; uric acid.

All sacrificed animals were completely dissected and photographically documented. Tumors (Prostatic gland) and metastases (Caudal, lumbar, renal lymph node metastases) were measured in two dimensions by means of a pair of callipers. The volume was calculated according to V $(mm^3)= ab^2/2$ with b<a. In general, the cell number performed for therapy approaches causes a 100% tumor take concerning the prostatic gland. The weights of some organs (Liver; Spleen; Kidney) were registered in order to find out additional data concerning the knowledge about secondary side effects.

For histological analysis samples of tumor tissues, i.e. prostate tumor and lymph node metastases, were fixed in 5% formaldehyde and paraffin embedded. Routinely, the sections were HE stained, if necessary specific stainings were made (Azan, PAS).

To detect the human origin of tumor and metastatic cells adequate tissue samples were frozen in liquid nitrogen. When using PCR and Taqman analysis with huHPRT specific amplicon we could detect 50 human cells in Smg tissue.

The therapeutic results were statistically verified by the u-test of Mann and Whitney.

EXAMPLE 2

Experimental Proof-Of-Concept on the Suitability of Downstream Drug Targets

As outlined in the introductory part of this specification which is incorporated herein by reference, targets linked downstream to a signalling pathway are valuable for the design or development of both medicaments and diagnostic agents. It is obvious that, if the particular target is linked to different other pathways or due to its position within the signalling pathway is linked to a number of biological phenomena such as, e.g. metastasis and migration, growth translation apoptosis, cell cycle, DNA repair and the like as in the case of PI-3 kinase, any compound addressing this target is likely to have a number of side effects which may be detrimental to the system and undesired from the medical point of view. Accordingly, targets that act further downstream should be the first choice for therapeutic intervention.

The present inventors have found that under the control of the PI 3-kinase pathway further possible drug targets apart from mTOR are involved, which are specific for controlling the phenomena of metastasis and migration and thus tumorigenesis. In the pharmaceutical industry it has been found that rapamycin, sold under the trade name of Rapamune is suitable to inhibit metastasis and migration. This confirms the suitability of the strategy to address downstream drug targets.

As may be taken from FIG. 2 rapamycin is suitable to reduce the volume of lymphnode metastasis and is insofar comparable in its effect to the well known PI 3-kinase inhibitor LY294002. As depicted in FIG. 2 A the tumor take model was used and treatment with Rapamune started on day 1. Both concentrations used, i.e. 0.4 mg/kg/dose-2 mg/kg/dose led to a tremendous decrease of the extent of lymphnode metastasis, expressed as measured volume of metastasis (mm$^3$) compared to the negative control which was phosphate buffered saline.

For histological analysis samples of tumor tissues, i.e. prostate tumor and lymph node metastases, were fixed in 5% formaldehyde and paraffin embedded. Routinely, the sections were HE stained, if necessary specific stainings were made (Azan, PAS).

The same results were basically also obtained in case of Rapamune treatment of an established tumor model with the treatment starting on day 28.

Lymph node metastasis in an orthotopic PC-3 mouse model after treatment with rapamycin (Rapamune) was measured. In FIG. 2 (A) the results of the (A), tumor take model are shown. Nude Shoe:NMRI—nu/nu mice (8 per group) were injected with 2×10$^6$ PC3 cells in 0.03 ml intraprostatic and treatment was carried out using Rapamune intraperitoneally daily for 28 days at doses of 2 mg/kg and 0.4 mg/kg. PBS served as a control.

For the treatment of established tumors (B), cells were allowed to grow ipros for 28 days and treatment was carried out orally using Rapamune on days 29 to 50 after implantation. Doses were chosen as outline in A. Animals were sacrificed on day 29 and 51, respectively and total lymph node metastasis were determined

EXAMPLE 3

Identification of PKN Beta as Downstream Drug Target Within the PI 3-Kinase Pathway The basic experimental approach is shown in FIG. 3. PC3 cells grown on Matrigel were either treated with DMSO or the PI 3-K inhibitor LY294002 and total RNA was isolated from each sample. Differential Affymetrix gene expression profiling was performed and expression was confirmned using real time RT-PCR Taqman assay. p110α was used as a non-differential standard. PC3 cells are PTEN −/− which means that the tumor suppressor PTEN is factually lacking in these cells so that the PI 3-kinase pathway is permanently activated which leads to an increased metastatic activity or behaviour of the cells which is expressed by their growth pattern in the matrigel assay. Cells with invasive growth potential exhibit enhanced growth on basement membrane such as matrigel matrix. (Petersen, O. W., Ronnov-Jessen, L., Howlett, A. R. and Bissell, M. J. (1992) Interaction with basement membrane serves to rapidly distinguish growth and differentiation pattern of normal and malignant human breast epithelial cells.

*Proc Natl Acad Sci USA*, 89, 9064-9068. (Auch: Stemberger et al., 2002 Antisense & Nucleic acid drug development 12:131-143)

In connection therewith it is to be noted that the PC3 cells were grown on matrigel and taken this as a model system which is close to the in vivo environment the RNA isolated therefrom is assumed to be closer to the in situ situation or results than any preparation obtained from cells grown in a non-matrigel environment such as a conventional cell culture plate.

EXAMPLE 4

Screening for Optimum Antisense Oligonucleotides Directed to Protein Kinase N Beta.

PC3 cells were transfected with different GeneBloc concentrations as described and mRNA levels were determined 24 hrs post transfection using Taqman assays with 300 nM of PKNbeta specific forward and reverse primer and 100 nM probe and 40 nM forward and reverse primer and 100 nM probe for human β-actin. mRNA levels are standardized to internal actin levels and amounts are shown relative to GBC (cells transfected with a Gene Bloc Control).

Figure 4:
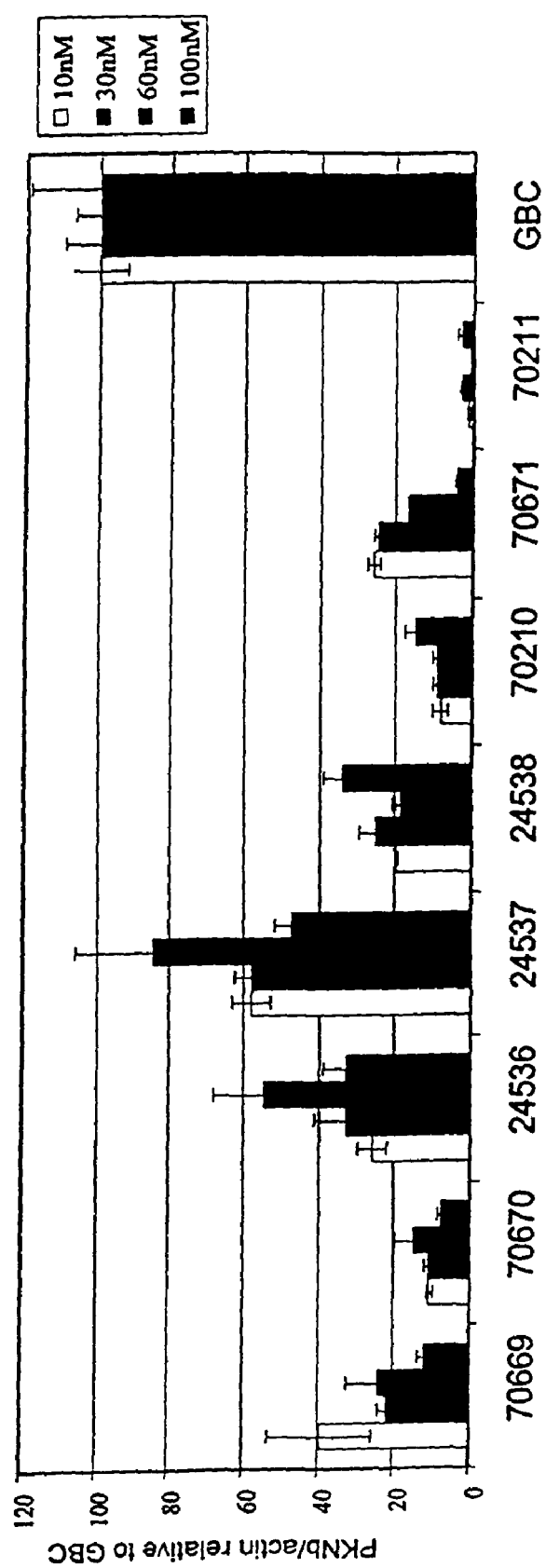
FIG. 4 shows a primary GeneBloc screen on PKNbeta.

The result thereof is shown in FIG. 4. From FIG. 4 as particularly advantageous antisense oligonucleotides GeneBlocs 70210 and 70211 were selected for further studies.

In connection with the GeneBloc as used herein in the various examples it is to be noted that they are all third generation antisense oligonucleotide as specified herein which means, as also obvious from table 1, that the upper case letters represent the deoxyribonucleotides which were linked through a phosphorothioate rather than a phosphodiester linkage

TABLE 1

Overview of the various GeneBlocs used, their alias, mismatches relative to the target nucleic acid and their sequence and structured characteristics

| GeneBloc No | Alias | MM | Sequence |
|---|---|---|---|
| 70669 | PKNbeta:706L21 | 0 | ggagguCCAGTTTCTgagagg |
| 70670 | PKNbeta:377L21 | 0 | uguuucACCTTCAGCuccaca |
| 24536 | PKNbeta:2021L23 | 0 | aggacaaCACAAGCCAcguagaa |
| 24537 | PKNbeta:2665L23 | 0 | gcucugaCACAAAGTCgaagucc |
| 24538 | PKNbeta:2322L23 | 0 | gcagucaAACACCTCTuccucug |
| 70210 | PKNbeta:1034L21 | 0 | caacacGGTTGTCCAccuuua |
| 70211 | PKNbeta:1784L21 | 0 | ucagugCTTTGATGGcguagu |
| 70671 | PKNbeta:183L21 | 0 | cuucucGCAGTACAGgcucuc |
| 70676 | PKNbeta:1034L21 | 4 | caagacGCTTGTGCAcguuua |
| 70677 | PKNbeta:1784L21 | 4 | ucagagCTTAGTTGGcguugu |

The various GeneBlocs correspond to the following SEQ. ID. Nos:

| 70669: | SEQ. ID. No. 3 |
| 70670: | SEQ. ID. No. 4 |
| 24536: | SEQ. ID. No. 5 |
| 24537: | SEQ. ID. No. 6 |
| 24538: | SEQ. ID. No. 7 |
| 70210: | SEQ. ID. No. 8 |
| 70211: | SEQ. ID. No. 9 |
| 70671: | SEQ. ID. No. 10 |
| 70676: | SEQ. ID. No. 11 |
| 70677: | SEQ. ID. No. 12 |

The above antisense oligonucleotides are GeneBlocs, i.e. third generation antisense oligonucleotides.

EXAMPLE 5

Selective Knock Down of Protein Kinase N Beta

In order to prove that protein kinase N beta is a suitable downstream drug target of the PI 3-kinase pathway the two particularly advantageous GeneBlocs as obtained from example 4 were used in a matrigel based growth experiment. The matrigel growth experiment is taken as a surrogate model which shows the metastasis and migration behaviour of the respective cell. A more confluent growth of the cells is taken as an indication that their metastasis and migration behaviour is increased which allows the cells to spread over the three-dimensional structure provided by the matrigel.

PC3 cells were transfected and seeded on matrigel as described and growth was monitored. siRNA was isolated from an aliquot of the cells seeded on matrigel and analysed using Taqman assay (left panel). PKNbeta specific mRNA was standardized to endogenous p110α mRNA levels. A PTEN specific GeneBloc is used as a negative control in the PTEN$^{-/-}$ PC-3 cells and a p110β specific GeneBloc is used as a positive control for growth in extracellular matrix. Specific growth inhibition is shown by comparing growth of cells treated with PKN beta specific GeneBloc 70210 or 70211 versus their corresponding mismatched oligonucleotides 70676 and 70677, respectively.

Figure 5:
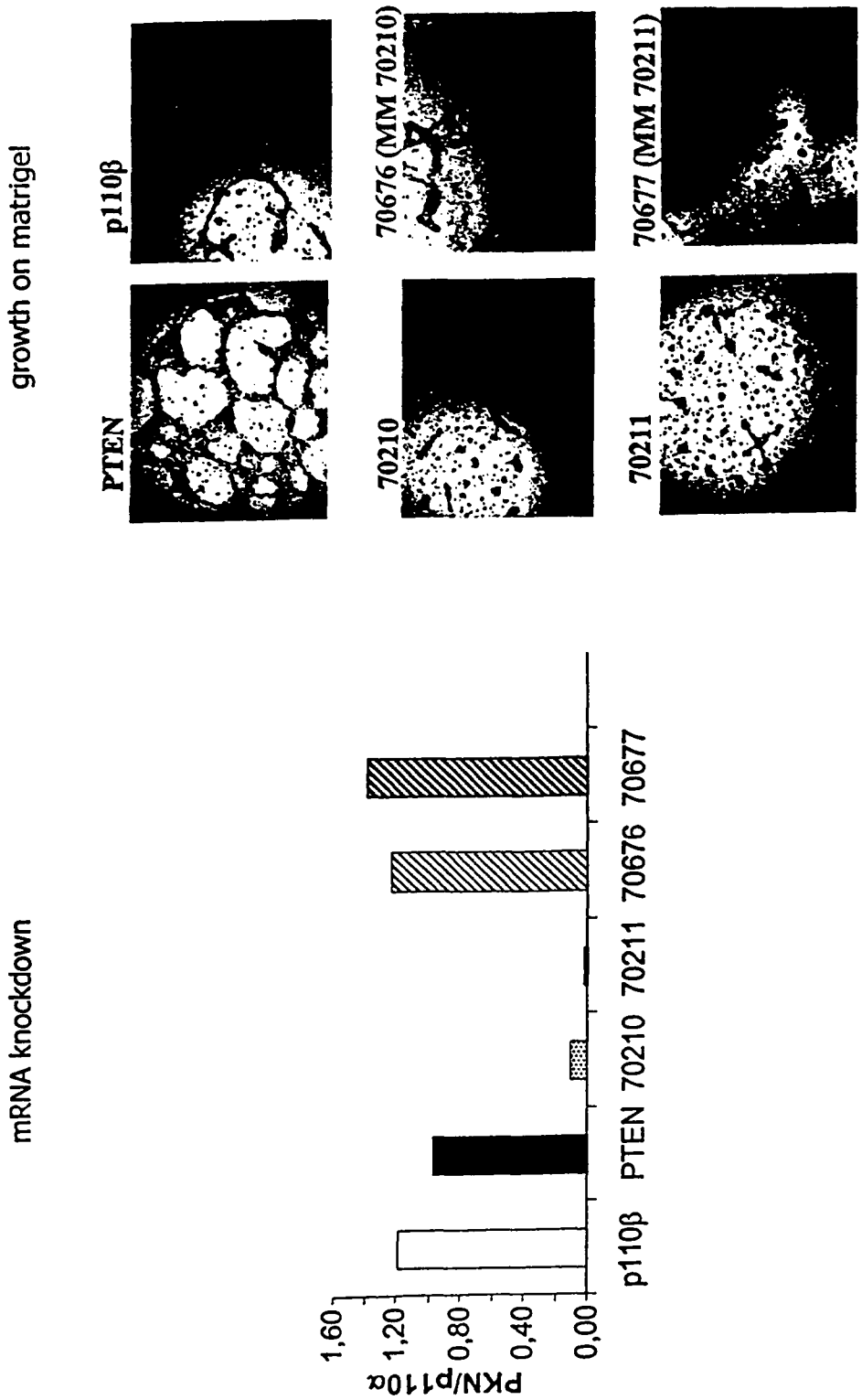
FIG. 5 shows the growth of PC3 cells transfected with PKNbeta specific GB on matrigel.

The respective results are also illustrated in FIG. 5. From this it may be taken that the gene block 70211 and 70210 may be suitable compounds for the manufacture of a medicament or diagnostic agent for the treatment of diseases and diseased conditions as described herein.

EXAMPLE 6

RNA Interference by Transient Expression of siRNA in HeLaB Cells

Figure 6:
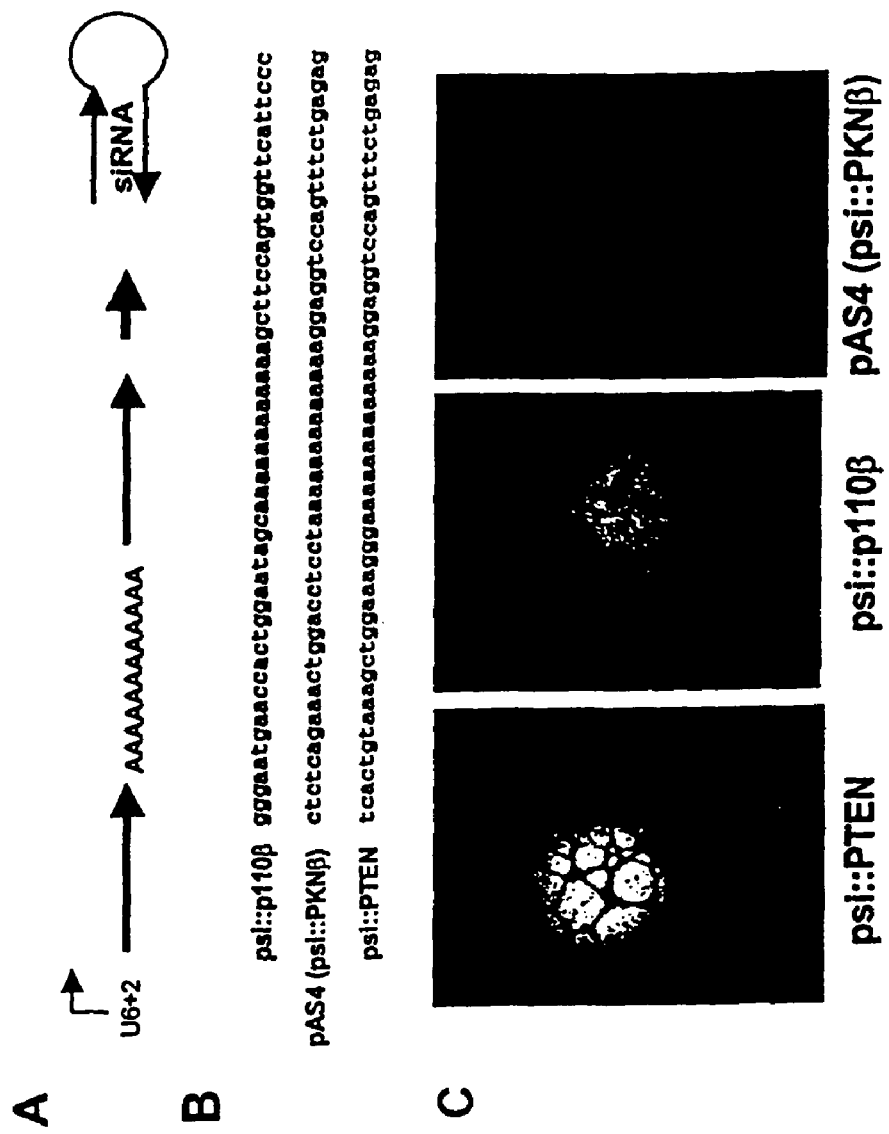
FIG. 6 shows RNA interference by transient expression of siRNA in HeLaB cells: (A) siRNA molecules were generated by promoter (U6+2) driven expression of target specific sequences (template derived from gene of interest containing a 21-mer sense and reverse complementary sequences linked by 12-mer poly A stretch (SEQ ID NO: 15). Upon transcription RNAs are likely to form double-stranded siRNA molecules; (B) Template sequences of targeted genes for siRNA expression (SEQ ID NOS: 16-18, respectively in order of appear). Corresponding sequence were introduced into expression vectors carrying the U6+2 promoter cassette; (C) Effect of siRNA expression on cell growth and proliferation. Constructs (see above) were transiently expressed by transfection in HeLaB cells for RNAi interference experiments. Cells were harvested 48 hour after transfected and subsequently seeded (80000 cells per well) on "matrigel" gel. The effect of RNA interference on the expression of corresponding genes was analyzed by assaying transfected cells for growth/proliferation on matrigel. Expression of siRNA targeted to PTEN had no affect on HeLaB cell growth on matrigel (right panel), whereas expression of siRNA specific to p110beta and PKNbeta severely disturbed the behaviour of HeLaB growth on matrigel (middle and right panels).

This experiment is an example of the successful design of siRNA which allows that specifically the downstream drug target protein kinase N beta is addressed. As illustrated in FIG. 6 (A) siRNA molecules were generated by promoter (U6+2) driven expression of target specific sequences (template derived from gene of interest containing a 21-mer sense and reverse complementary sequences linked by 12-mer poly A stretch. Upon transcription RNAs are likely to form double-stranded siRNA molecules.

The various constructs such as p110beta and PTEN were used as positive and negative control, respectively in the same vector construct as the siRNA designed against the mRNA sequence of PKNbeta. The respective design is shown in FIG. 6 (B) were the template sequences of targeted genes for siRNA expression were introduced into expression vectors carrying the U6+2 promoter cassette.

The constructs were transiently expressed by transfection into HeLaB cells for RNAi interference experiments. Cells were harvested 48 hour after transfected and subsequently seeded (80000 cells per well) on matrigel. The effect of RNA interference on the expression of corresponding genes was analyzed by assaying transfected cells for growth/proliferation on matrigel. Expression of siRNA targeted to PTEN had no affect on HeLaB cell growth on matrigel (right panel), whereas expression of siRNA specific to p110beta and PKN-beta severely disturbed the behaviour of HeLaB growth on matrigel (middle and right panels).

In view of this, the particular siRNA sequence proves to be an efficient means for the treatment of the disease and disease conditions as disclosed herein.

EXAMPLE 7

Detection of Protein Kinase N Beta in Human Prostate Tumor

In order to give further evidence that protein kinase N beta is a suitable target in the treatment of prostate tumor, respective human prostate tissue was subjected to in situ hybridisation.

For the in situ hybridisation both sense and antisense strands were prepared from nucleotide positions 1672 to 2667 from sequence NM 013355 in pCR4 Topo vector, whereupon T7 and T3 polymerase was used for amplification purposes. The human prostate tumor cells (PC-3) were grown in mice. After dissection, the tissue was frozen at −20° C. in isopentane solution, slices cut at −15° C. and stored at −80° C. Prior to hybridisation slices were fixed in paraformaldehyde. Human tumor specimen were fixed in paraformaldehyde and paraffine-embedded. Tumor specimens were treated with proteinase K and acetylated. Nucleic acid probes were double-labelled with $^{35}$S-ATP and $^{35}$S-UTP and incubated with tissues at 58° C. in a hybridisation buffer (0.4 M NaCl, 50% formamide, 1× Denhardt's, 10 mM Tris, 1 mM_EDTA, 10% dextran sulfate, 10 µg/ml of each tRNA and salmon sperm DNA, 10 mM DTT) containing 50% formamide.

Figure 7:
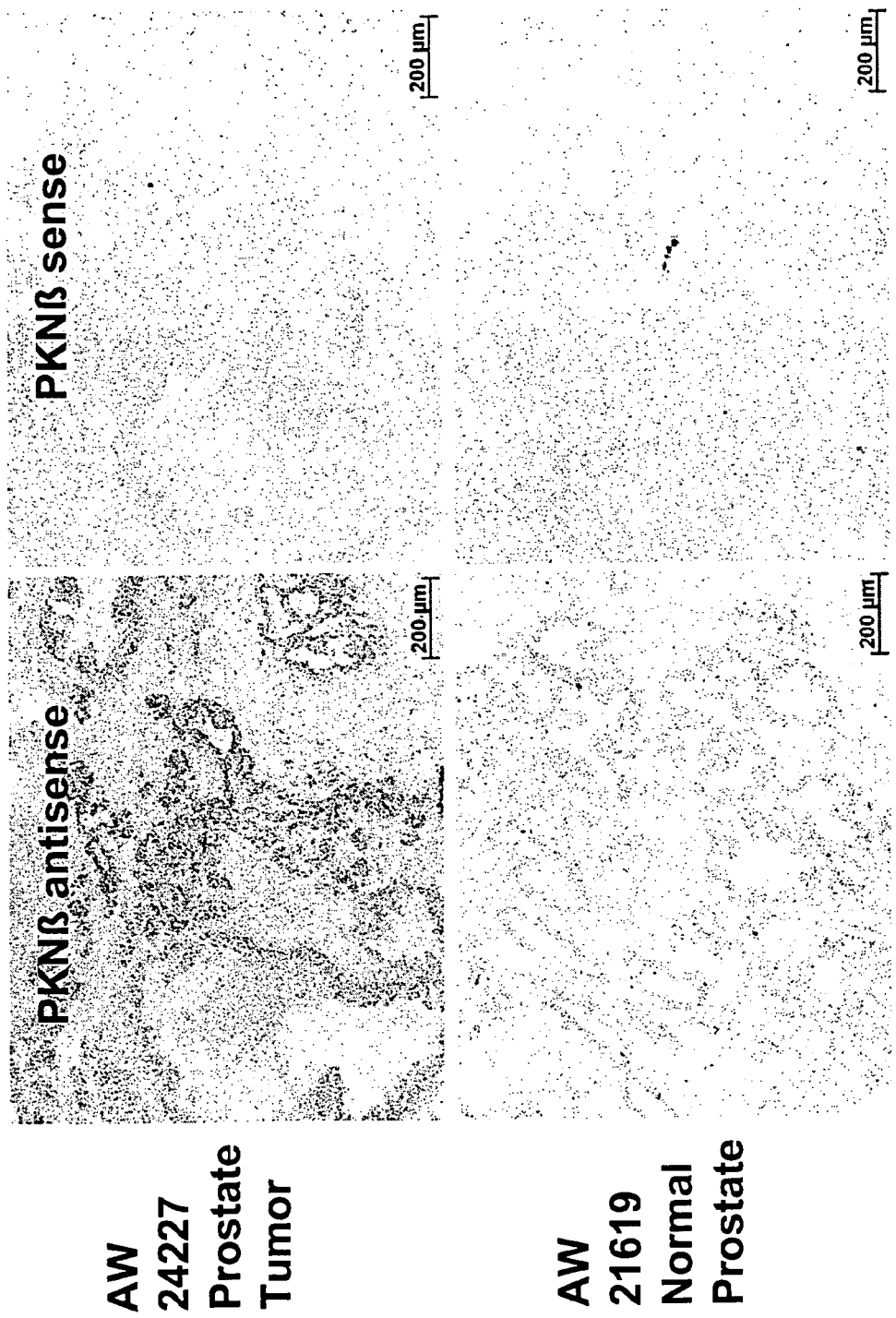
FIG. 7 shows photographs of human prostate cells and human prostate cancer cells upon hybridisation using protein kinase N beta antisense and sense sequences as probes.

The result of the in situ hybridisation is depicted in FIG. 7. Using protein kinase N beta antisense probe for in situ hybridisation of prostate tumor the glands are intensively stained (FIG. 7A). In contrast to this, healthy prostate tissue is less stained and provides for a background signal only, again using the antisense probe (FIG. 7C). In contrast to this, the use of the sense probe in connection with both tissues, did not provide any signal.

EXAMPLE 8

In Vivo Reduction of Primary Tumor and Lymph Node Metastases by siRNA

This example is related to target gene validation in vivo using an orthotopic prostate tumor model in which it could be shown that by using siRNA directed to protein kinase N beta a reduction of both primary tumor and lymph node metastases could be realised. The results are depicted in FIGS. 8A to 8C.

Figure 8:
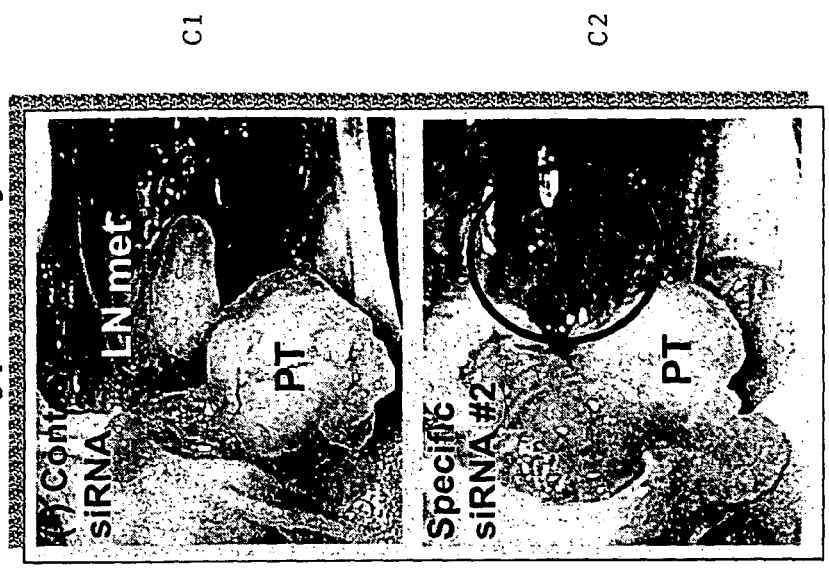
FIG. 8 shows a diagram depicting the volume of primary tumors in an orthotopic prostate tumor model using two different siRNA constructs (FIG. 8A), a diagram depicting the volume-of lymph node metastases in an orthotopic prostate tumor model using two different siRNA constructs (FIG. 8B), and photographs of prostate and lymph nodes in an orthotopic prostate tumor model using control siRNA (FIG. 8C1) and a protein kinase N beta specific siRNA construct (FIG. 8C2)
Figure 8:
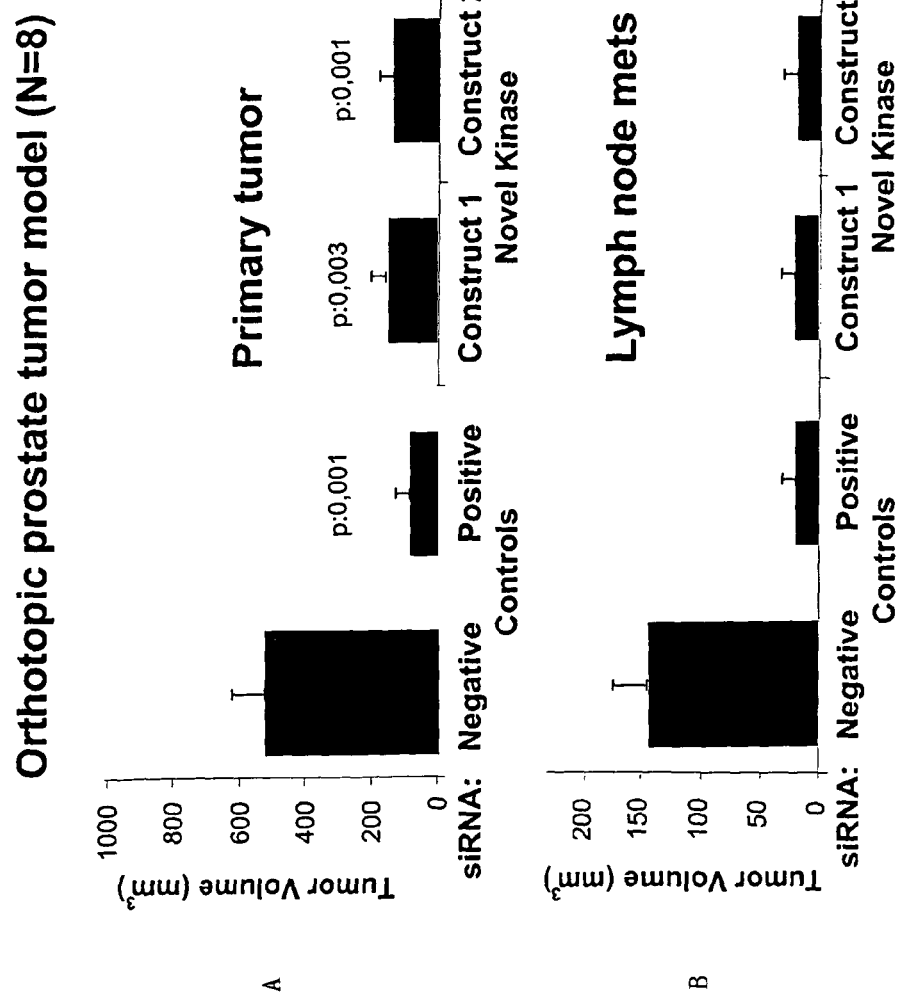

In the diagram of FIG. 8A the volume of primary tumors, determined as described in example 1, in an orthotopic prostate tumor model could be significantly reduced using any of the following two siRNA constructs:

```
5' actgagcaagaggctttggag    (SEQ ID NO: 13)
or

5' aaattccagtggttcattcca.   (SEQ ID NO: 14)
```

As negative control siRNA against p110-α subunit was used and as positive control siRNA against p110-β subunit. The positive control thus addresses the upstream regulator of protein kinase N beta PTEN.

A further set of two independent siRNA molecules was used for degrading the MRNA encoding for protein kinase N beta in lymph node metastases. Lymph node metastases are secondary tumors found in the following lymph nodes: Caudal, Lumbar, Renal and mediastinal lymph nodes whereby caudal lymph nodes are closest to the prostate and mediastinal lymph nodes are most distant to the implantation tumor. As in the case of the primary tumor, the siRNA constructs were obviously successfully reducing the mRNA coding for protein kinase N beta and thus reducing the tumor volume (FIG. 8B). Positive and negative controls were as discussed in connection with the reduction of primary tumor.

In both cases, i.e. for primary tumor and lymph node metastases, the human prostate tumor cells were genetically engineered to express the respective siRNA molecules from a polymerase III U6 promoter.

Apart from these results, a clear phenotypic analysis as depicted in FIG. 8C1 and FIG. 8C2 shows that upon activation of the transcription of the siRNA construct in the human prostate tumor cells, lymph node metastases could be significantly reduced and the swollen lymph node depicted in FIG. 8C1 is not present in the tissue treated with siRNA as depicted in FIG. 8C2.

EXAMPLE 9

Functional Characterisation of the Protein Kinase N Beta

This example is related to the functional characterisation of protein kinase N beta and more particularly to the impact of derivatisation, i.e. truncation or mutation of fluctional amino acid residues, of protein kinase N beta on its kinase activity and on the regulation of its kinase activity by phosphorylation.

The following protein kinase N beta derivatives were generated as also at least partially depicted schematically in FIG. 9C with the amino acid residues referring to the wild type sequence as disclosed herein:

a) kinase domain comprising amino acids 535-889;

b) αN comprising amino acids 288-889;

c) kinase domain having a mutation at position 588 from lysine to arginine;

d) kinase domain having a mutation at position 588 from lysine to glutamic acid;

derivatives of the kinase domain having mutations at the phosphorylation site (AGC activation loop consensus) with the threonine residue at amino acid position 718 being either changed to alanine (TA718) or to aspartic acid or glutamic acid (TD718 or TE718); and full length wildtype PKNbeta molecule (889 amino acids).

The respective fragments were transiently epressed in HeLa cells. Their relative expression was determined by Western-blot analysis of Hela cell extracts using an anti-PKNbeta antibody.

The polyclonal anti-PKNbeta antiserum was generated after overexpressing the C-terminal amino acids (609-889)of PKNbeta in *E. coli*. The respective protein fragment was gel-purified from inclusion bodies, recovered and concentrated according to standard procedures.

Protein kinase N beta has homologies to AGC-type kinase molecules in its catalytic domain at the C-terminus. The family of kinases is characterised by a conserved threonine residue in the activation loop of the catalytic domain that needs to be phosphorylated for enzymatic activity. Due to the high conservation of this threonine and the surrounding amino acid context in the activation loop, anti-phospho antibodies against this site are available from commercial sources. The respective antibodies are referred to as anit-P*-PRK in FIG. 9 and as anti-P*-AGC kinase in FIG. 10.

MPB is myelin basic protein which is a standard in vitro phosphorylation substrate.

The following results were obtained:

| Protein kinase N beta derivative | Activity |
|---|---|
| Full length wt | ++* |
| Kinase domain comprising amino acids 535-889 | +* |
| ΔN comprising amino acids 288-889 | −* |
| Kinase domain having a mutation at position 588 from lysine to arginine (KR 588) | −* |
| Kinase domain having a mutation at position 588 from lysine to glutamic acid (KE 588) | −* |
| TA718 | −* |
| TD718 or TE718 | −*! |

*+: active
−: inactive
!: no "hyper activation" was observed as one might have expected from comparable mutations in other kinases (Morgan and Debond, 1994)

Figure 9:
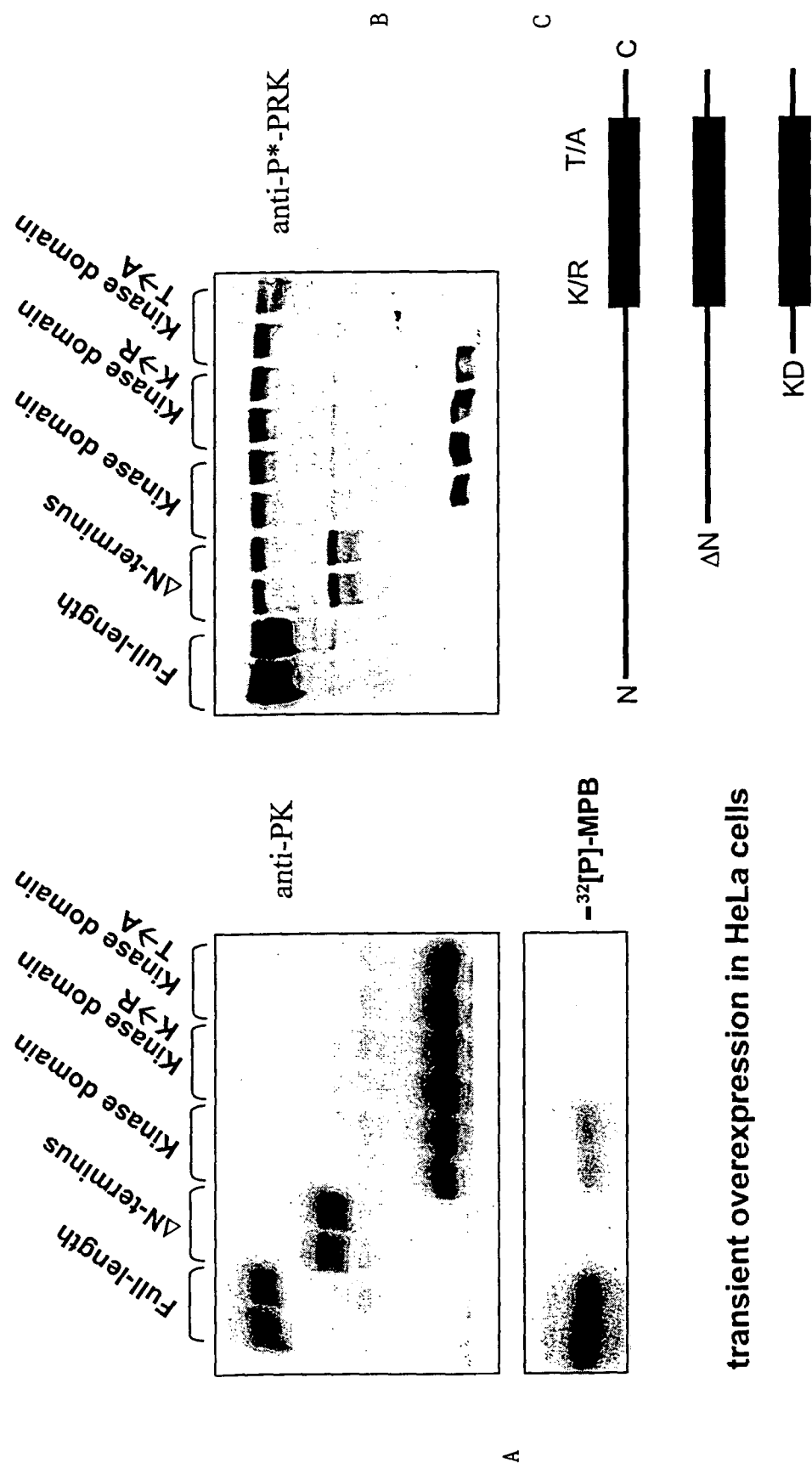
FIG. 9 shows a Western-blot analysis of different protein kinase N beta derivatives and their activities using MPB as a standard phosphorylation substrate upon transient overexpression in HeLa cells and anti-protein kinase N beta antibody (anti-PK) for detecting the relative expression levels of the kinase derivatives (FIG. 9A), a further Western-blot analysis of different protein kinase N beta derivatives using an antibody specific for the phosphorylated form of protein kinase N beta (FIG. 9B), and a schematic representation of the various protein kinase N beta derivatives used (FIG. 9C)

The results are depicted in FIG. 9.

FIG. 9A shows a gel analysis of different protein kinase N beta derivatives and their activities using MPB as a standard phosphorylation substrate upon transient overexpression in HeLa cells. As may be taken from FIG. 9A apart from the full-length protein kinase N beta only the kinase domain in its otherwise wildtype form is active in phosphorylating MPB.

Using the same protein kinase N beta derivatives it can be observed that except the derivative comprising kinase domain having the mutation T/A at position 718, all other derivatives displayed were also phosphorylated regardless of their further intrinsic activities.

The data indicates that the presence of a functional kinase domain and phosphorylation at position 718 are pre-requisites for PKNbeta kinase activity. However, as can be concluded from the inability of the AN version to act as a kinase, they are not sufficient. The data also indicates that PKNbeta does not autophosphorylate at amino acid 718, but instead, requires phosphorylation by another kinase molecule, since the kinase defective KR588 mutant protein retains phosphorylation at position 718.

EXAMPLE 10

Characterization of Full Length PKNbeta

Figure 10:
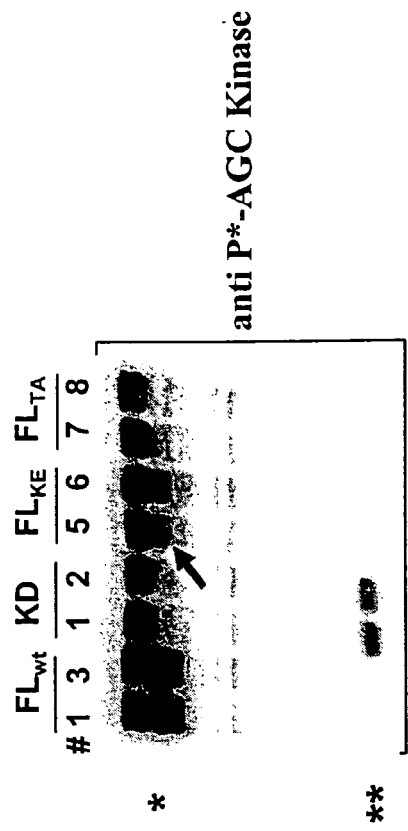
FIG. 10 shows a Western Blot of various protein kinase N beta derivatives (FIG. 10A) to monitor the expression levels thereof in HeLa cells and a gel analysis of the phosphorylation of the protein kinase N beta derivatives (FIG. 10B)
Figure 10:
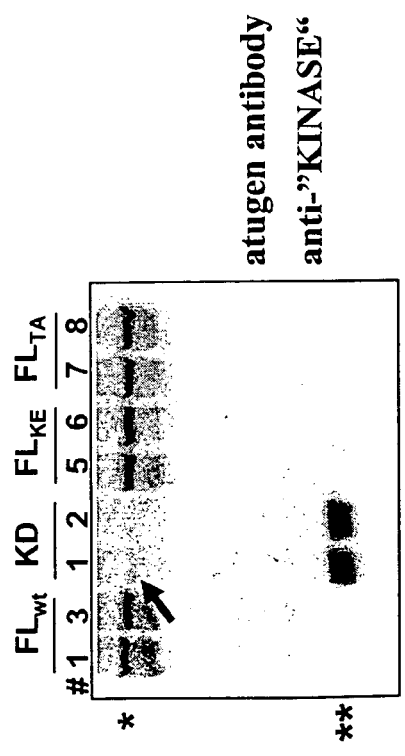

In order to analyse mutations of functional amino acid residues of protein kinase N beta in the context of the full length molecule, the following experiments were carried out as shown in FIGS. 10 and 11:

For measuring the kinase activity of PKNbeta in vitro, recombinant HA- or Myc-tagged PKNbeta derivatives were transiently expressed in HeLa or COS-7 cells. The smaller kinase domain derivative served as a control. The cell extracts containing the recombinant versions of protein kinase N beta were probed in parallel with anti-protein kinase N-beta antibody (FIG. 10A) as described in example 9 to demonstrate comparable expression levels, and an anti-phospho AGC site antibody (also referred to as anti-P*-AGC-kinase) (FIG. 10B) to show the different degree of phosphorylation of the protein kinase N beta derivatives in vivo.

EXAMPLE 11

Phosphorylation Requirements for the Activity of Full Length Protein Kinase N Beta and Development of a Non-Radioactive In-Vitro-Kinase Assay—Suitability of Protein Kinase N Beta for HTS Assays The PKNbeta-derived molecules were immune-precipitated from the cell extracts shown in FIG. 10 by using anti-tag antibodies. The immune precipitates were washed as described (Klippel et al., 1996) and divided in two halfs. One half was incubated with 5 µg MBP (UBI) as a phosphorylation substrate, 4 mM $MgCl_2$ and gamma $^{32}$P-ATP in a buffered solution for 10 min at room temperature. In addition, phosphatase inhibitors and inhibitors against unspecifically acting kinases were added as in Klippel et al., 1998. Incorporation of radioactive phosphate was detected by autoradiography after separating the reaction products by 16% SDS-PAGE (FIG. 11B).

The second half of the immune precipitates was incubated with 1 µg GST-GSK3 fusion protein (Cell Signaling Technology) as a phosphorylation substrate in the presence of 200 µM rATP. The reaction mixture was subsequently analyzed by 8-16% gradient SDS-PAGE and Western blotting using the anti-phospho GSK3alpha antibody (Cell Signaling Technology) (FIG. 11A). The filter was then stripped and re-probed with anti-PKNbeta antiserum to confirm the presence of comparable amounts of PKNbeta proteins in the respective immune precipitates (FIG. 11C).

The specificity of the in vitro phosphorylation reactions was controlled by analyzing kinase defective variants (e.g. containing mutations in the ATP binding site, see above) in parallel to active protein.

The lack of signal in case of the TA mutation variant at amino acid 718 of protein kinase N beta otherwise being the full length wildtype protein kinase N beta indicates that this amino acid residue is indeed the position of phosphorylation detected by the antibody (FIG. 10B). The fact that the kinase deficient variants (KE or KR mutation as shown in FIG. 10 and FIG. 9, respectively) are phosphorylated at this site indicates that threonine 718 is not a substrate for autophosphorylation. Rather another kinase in the cells must be responsible for phosphorylation of this site; whereby PDK1 is a possible candidate.

Also, from this experiment in combination with the one of example 9 it is revealed that phosphorylation of protein kinase N beta at position 718 is pre-requisite for protein kinase N beta activity; all mutations tested at this site prevented phosphorylation and resulted in an inactive kinase molecule. Insofar a particularly preferred protein kinase N beta which can be used in connection with any aspects of the invention as disclosed herein is a protein kinase N beta being phosphorylated at position 718 or a derivative thereof, including the derivative which comprises the kinase domain only as described herein. The data further indicates that also full length PKNbeta does not autophosphorylate at amino acid 718, but instead, requires phosphorylation by another kinase molecule, since the kinase defective KE588 mutant protein retains phosphorylation at position 718.

As may be taken from FIG. 11, assaying the activity of protein kinase N beta can be adapted into a format which allows the screening of protein kinase N beta inhibitors into a high throughput system.

In a first step, the suitability of a non-radioactive screening formate was determined, whereby the various protein kinase N beta derivatives as already discussed in connection with example 10, were used for phosphorylating a suitable substrate. Such substrate may, for example, be MBP or a GSK3 peptide which is typically immobilised on a suitable carrier such as agarose- or sepharose beads or on plastic surfaces. In the present case and as depicted in FIG. 11A, the substrate is a GSK3-derived peptide fused to paramyosin. The first row indicates that all of the various assays using different protein kinase N beta derivatives actually contained said derivatives. Only the full length wildtype protein kinase N beta or the kinase domain as defined in example 9 were suitable to phosphorylate the substrate. The phosphorylated substrate in the present case was detected by anti-phospho GSK3 alpha antibody (mentioned above).

To make sure that the non-radioactive approach as depicted in FIG. 11A is sensitive enough the radioactive approach was carried out in parallel with half of the immune precipitates using the MBP as a phosphorylation substrate. The efficacy of the kinase activity can be taken from the amount of the generated phosphorylated substrate as indicated by autoradiography upon [$^{32}$P] incorporation. As can be seen from FIGS. 11A and 11B, the full length wildtype protein kinase N beta as well as the kinase domain show activity, whereas no (FIG. 11A) or background activity of unspecific kinases (FIG. 11B) were detected with the full length KE and full length TA mutatant proteinss, respectively.

To summarise, the use of both full length wildtype protein kinase N beta as well as the kinase domain as disclosed herein, are suitable targets or means for the design of a screening procedure in HTS format. The respective steps would accordingly comprise a) generating purified recombinant protein kinase N beta protein by expression in a non-bacterial expression system such as insect cell system (example for different kinase in Klippel et al., 1997) in view of the fact that the protein needs to be phosphorylated for exhibiting kinase activity, which cannot easily be accomplished by expression in bacterial systems;

b) immobilisation of GSK3-derived substrate or similar substrate, and incubating the substrate with purified protein kinase N beta in the presence of rATP, $MgCl_2$ and inhibitors in a buffered solution;

c) detecting phosphorylation of the substrate by an appropriate detection means such as an antibody like the anti-phopho-GSK3 antibody optionally upon after serial washes and further optionally subsequently developing in Delfia or Lance assay systems (Perkin Elmer), whereby the phosphorylation site is bound by a Europium-labelled antibody. The amount of bound Europium is then quantitated by time-resolved fluorescence analysis.

EXAMPLE 12

Determination of the Expression Level of Endogenous PKN-Beta

In this example experimental evidence is given that PKN-beta is expressed in a P13-kinase dependent manner. The PI 3-kinase-dependent expression of PKNbeta RNA shown in FIG. 3 is here further confirmed on protein level.

PC-3 cells were cultivated as described in example 1 herein. Said PC-3 cells are PTEN −/−. HeLa cells were obtained from the American Type Culture Collection (ATCC) and grown as described in Sternberger et al. (2002). Transfections were carried out in 10-cm plates (at 30% to 50% confluency) using Fugene 6 (Roche, Nutley, N.J.) according to the manufacturer's instructions. Cultivated cells were trypsinated and harvested following stopping the trypsin effect by medium.

Both cell types, i.e. PC-3 cells and HeLa cells were treated for the indicated times with 10 μM LY294002 or DMSO, whereby DMSO was used as the solvent for LY294002 and, because of this, as negative control.

The resulting extracts were fractionated by SDS-PAGE and subsequently analysed by Western-blotting. The levels of the indicated proteins such as p110, which served as a loading control, endogenous PKN-beta and phosphorylated Akt were detected using the respective antibodies. Phosphorylated Akt (P*-Akt) serves as a control for the efficacy of the LY294002-mediated treatment.

Figure 12:
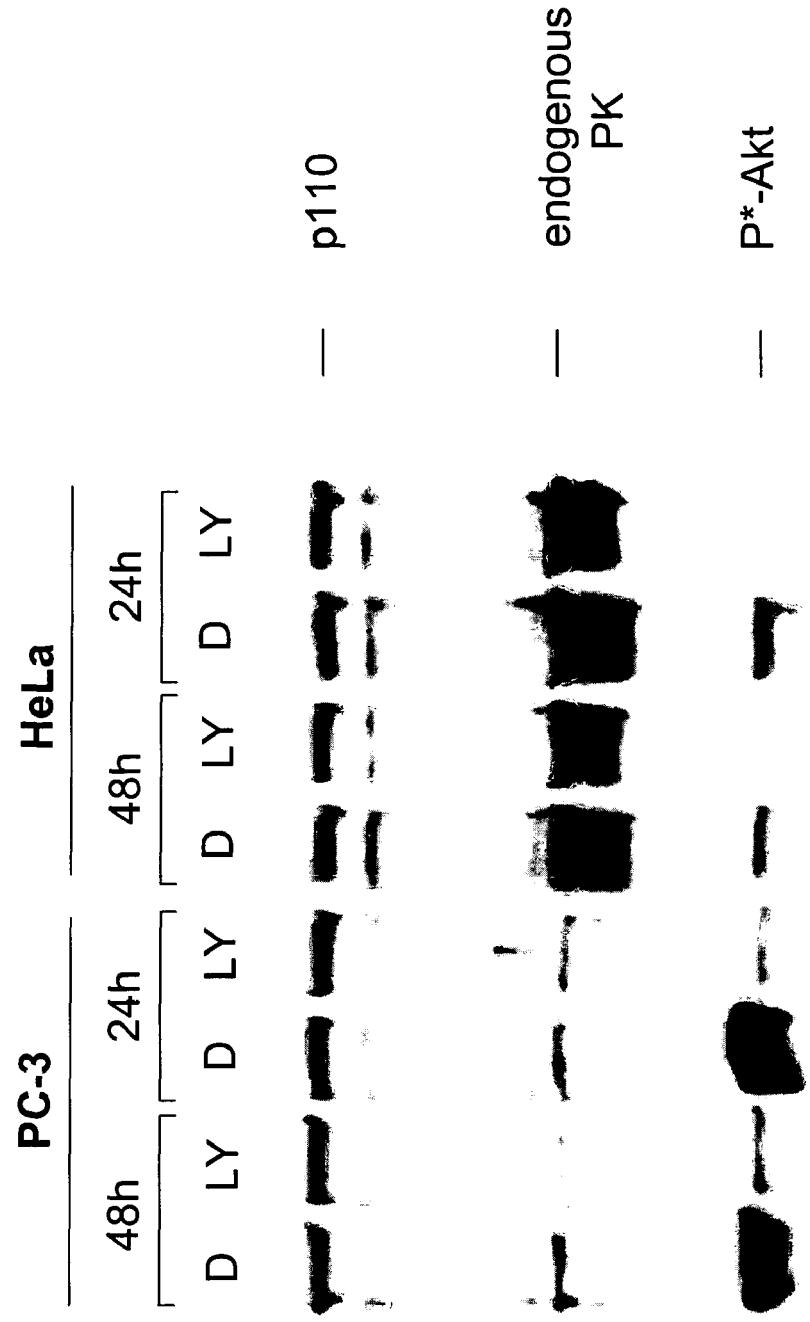
FIG. 12 shows a Western Blot analysis comparing the expression of endogenous protein kinase N beta in samples that were treated with LY294002 for different times in HeLa and PC-3 cells. The level of phosphorylated AKT was monitored in parallel to confirm efficacy of the PI 3-kinase inhibitor.

The results are depicted in FIG. 12.

In PC-3 cells inhibition of PI-3-kinase caused a visible reduction of endogenous PKNbeta expression after 24 h, the protein levels were further reduced after 48 h treatment. In HeLa cells, which express higher amounts of PKNbeta protein, this effect is less dramatic, but reduced amounts can be detected after 48 h treatment with LY294002.

From this it can be concluded, that P13-kinase controls the expression of PKN-beta.

EXAMPLE 13

PKN-Beta Activity Requires P13-Kinase

Recombinant wildtype PKN-beta or derivatives of PKN-beta (as described in FIGS. 10-11) were transiently expressed in HeLa cells. Said derivatives were PKN-beta derivative TA and derivative KE as described in example 10 herein. The PKN-beta was modified in each case by a myc-tag as described above which allowed the precipitation of PKN-beta and its derivatives using an anti-Myc antibody.

For the assessment of the activity of PKN-beta an in vitro kinase activity using the immune precipitates was carried out as described above. Half of the precipitates were subjected to the in vitro kinase reaction, the second half was analyzed by Western-blotting using anti-phospho-PRK antibodies. The filter was stripped and reprobed using the anti-PKN-beta antiserum. Phospho-p70 S6 Kinase levels were analyzed from aliquots of cell lysates, that were withdrawn earlier, to confirm the efficacy of the LY294002 treatment even after only 3 h treatment. The anti-phospho p70 antibody was obtained from Cell signaling.

Figure 13:
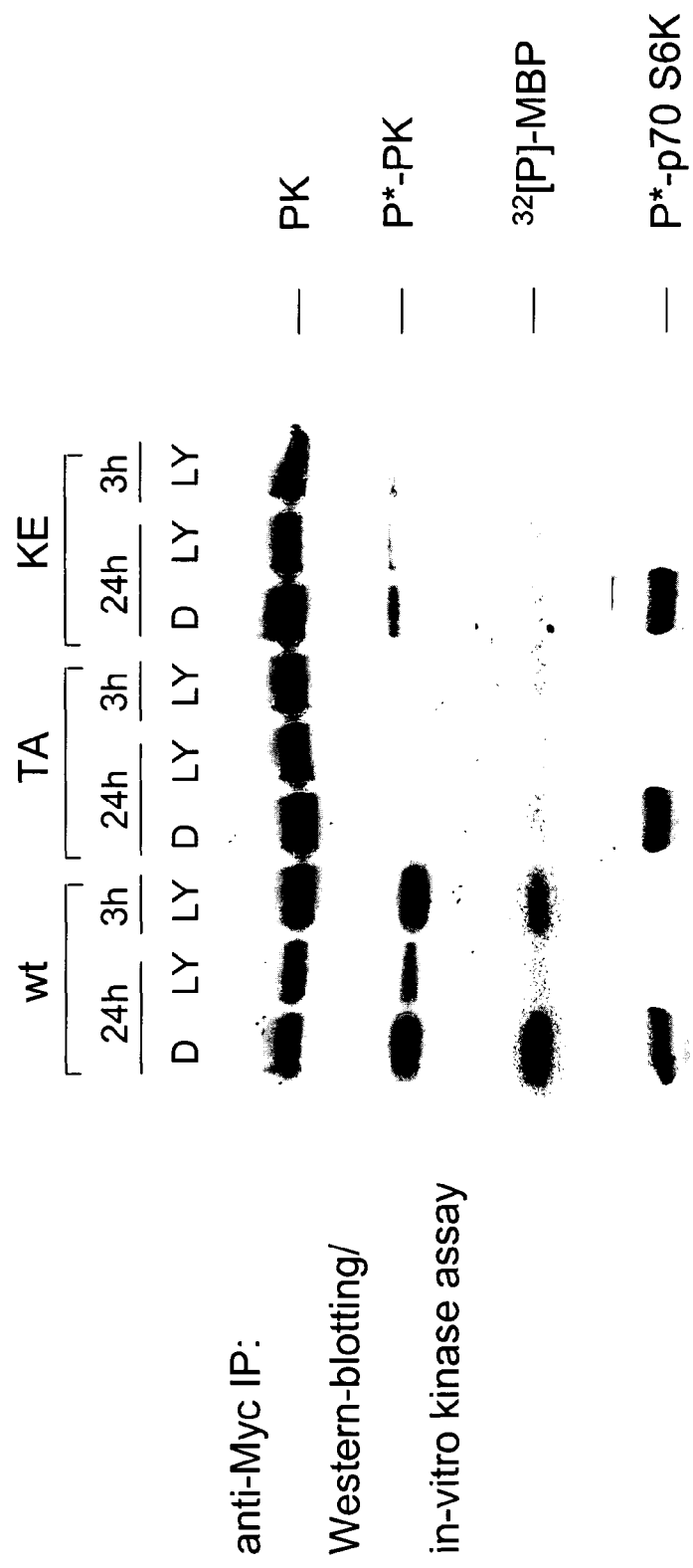
FIG. 13 shows the relative protein amounts and kinase activities of various recombinant PKNbeta derivatives present in immuno-complexes. The cells expressing the respective recombinant proteins had been treated with he PI 3-kinase inhibitor LY294002 prior to lysis for the indicated times.

As can be seen from FIG. 13 LY294002 treatment leads to strong inhibition of the kinase activity of PKNbeta, measured here again by phosphorylation of MBP. This effect was visible after only 3 h of treatment, at 24 h PKNbeta activity was almost completely inhibited. The phosphorylation of PKN-beta at position 718 was also compromised after inhibition of PI 3-kinase by LY294002, however, this effect was less pronounced than the effect on the kinase activity.

The TA derivative of PKN-beta serves as inactive control as shown above, and as control for the specificity of the anti-phospho PRK antibody for phospho-threonine at position 718 (P*-PK)

PKN-beta derivative KE serves as kinase-deficient control as described above. Its phosphorylation status appeared also to some extent affected by LY294002 treatment. This indicates that the kinase, which is responsible for phosphorylating PKNbeta at position 718, does so in a PI 3-kinase-dependent fashion.

Most importantly, this experiment shows that PKNbeta is not only regulated by PI 3-kinase via its expression level (see FIGS. 3 and 12), it is also regulated at its activation level. These findings indicate that PKNbeta represents a "perfect" downstream target for interference with a hyperactive PI 3-kinase pathway for therapeutic intervention, since it is equisitely dependent on PI 3-kinase being regulated by it at various levels. This allows the generation of compounds which exhibit a distinct effect on both the protein PKN-beta and the nucleic acid coding therefor. Even more important, this kind of activity modulation of PKN-beta at the translation rather than transcription level, i.e. at the level of the expressed protein, seems to be more prominent and longer lasting than the impact at the transcription level.

The further screening method according to the present invention is based on this particular insight and uses preferably the radioactive or nonradioactive in vitro kinase assay as read-out.

EXAMPLE 14

Localization Signals of PKN-Beta

Figure 14:
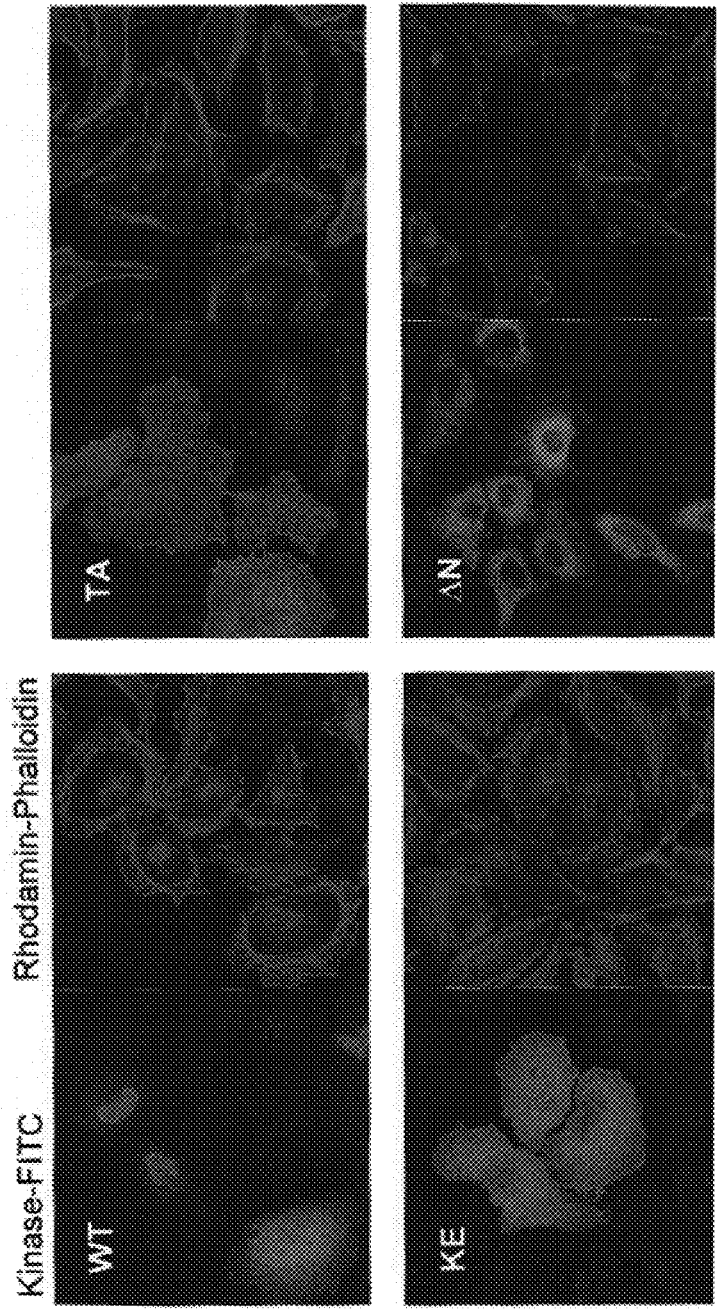
FIG. 14 shows a panel of pictures, whereby the cellular distribution of PKN beta and derivatives thereof such as PKN beta wildtype (FIG. 14A), PKN beta derivative TA (FIG. 14B), PKN beta derivative KE (FIG. 14C) and PKN beta deltaN (FIG. 14D) was investigated by confocal fluorescence microscopy. HA-tagged recombinant derivatives of PKNbeta were transiently expressed in HeLa cells for 48 h. After fixing and permeabilization, expression of the recombinant proteins was detected by using an anti-HA antibody followed by an FITC-conjugated anti-mouse antibody. The cells were counterstained by labelling the cytoskeletal actin with rhodamin-phalloidin.

In this experiment the localization of various PKN-beta derivatives was compared to the localization of wildtype PKN-beta. FIG. 14 shows pictures, whereby the cellular distribution of PKNbeta and derivatives thereof such as PKN beta wildtype (FIG. 14A), PKN beta derivative TA (FIG. 14B), PKN beta derivative KE (FIG. 14C) and PKN beta deltaN (FIG. 14D) was investigated by confocal fluorescence microscopy. HA-tagged recombinant derivatives of PKNbeta were transiently expressed in HeLa cells for 48 h. After fixing and perneabilization, expression of the recombinant proteins was detected by using an anti-HA antibody followed by an FITC-conjugated anti-mouse antibody. The cells were counterstained by labelling the cytoskeletal actin with rhodamin-phalloidin.

The results are depicted in FIGS. 14A to 14D, whereby the respective picture on each left side of the duplex of the pictures is related to a picture of cells upon FITC-specific excitation and the right picture illustrates the same cells upon excitation using a wavelength specific for Rhodamin-phalloidin. The FITC-staining indicates cells transfected with the respective recombinant protein. The Rhodamin-phalloidin staining shows transfected and unstransfected cells.

As may be taken from FIG. 14A, wildtype PKN-beta localizes predominantly to the nucleus of the cells. The phosphorylation site mutant of PKN-beta TA and the KE mutant, both are kinase-deficient, are no longer concentrated within the nucleus compared to wildtype PKN-beta, but rather spread over the entire cell. Finally, as depicted in FIG. 14D the PKN-beta derivative ΔN, which lacks the N-terminal third of the molecule and is also kinase-defective (see FIG. 9), is essentially excluded from the nucleus.

These data indicate that proper nuclear localization of PKNbeta to the nucleus is dependent on its ability to act as an active kinase molecule and involves the presence of its N-terminal domain. This implicates that PI-3 kinase might regulate also its cellular localization.

The features of the present invention disclosed in the specification, the sequence listing, the claims and/or the drawings may both separately and in any combination thereof be material for realizing the invention in various forms thereof.

What is claimed is:

1. A method of treating adenocarcinoma comprising administering to a subject having adenocarcinoma an effective amount of a composition comprising an siRNA molecule or an antisense oligonucleotide that inhibits the activity of protein kinase N beta by causing degradation of a ribonucleic acid encoding protein kinase N beta, wherein protein kinase N beta is up-regulated in adenocarcinoma cells as compared to non-tumor cells of the same lineage.

2. The method according to claim 1, wherein said siRNA molecule comprises SEQ ID NO: 13 or SEQ ID NO: 14.

3. The method according to claim 1, wherein said composition comprises an antisense oligonucleotide.

4. The method according to claim 1, wherein said composition comprises a siRNA molecule.

5. A method of inhibiting or reducing the metastasis or migration of a tumor cell or a hyperplastic cell comprising administering to a subject a composition comprising an siRNA molecule or an antisense oligonucleotide in an amount effective to inhibit the metastasis or migration of said tumor cell or hyperplastic cell, wherein said siRNA molecule or antisense oligonucleotide molecule inhibits the activity of protein kinase N beta by causing degradation of a ribonucleic acid encoding protein kinase N beta and wherein protein kinase N beta is up-regulated in said tumor cell or hyperplastic cell as compared to non-tumor cells or non-hyperplastic cells of the same lineage.

6. The method according to claim 5, wherein said composition comprises an antisense oligonucleotide.

7. The method according to claim 5, wherein said composition comprises an siRNA molecule.

8. The method according to claim 5, wherein said tumor cell or hyperplastic cell is an endometrial cancer cell; a colorectal carcinoma cell; a glioma cell; an adenocarcinoma cell; an endometrial cell displaying hyperplasia; a breast cancer cell; a thyroid cancer cell; an ovarian cancer cell; or a prostate cancer cell.

9. The method according to claim 8, wherein said tumor cell is an endometrial cancer cell.

10. The method according to claim 8, wherein said tumor cell is a colorectal carcinoma cell.

11. The method according to claim 8, wherein said tumor cell is a glioma cell.

12. The method according to claim 8, wherein said tumor cell is an adenocarcinoma cell.

13. The method according to claim 8, wherein said hyperplastic cell is an endometrial cell displaying hyperplasia.

14. The method according to claim 8, wherein said tumor cell is a breast cancer cell.

15. The method according to claim 8, wherein said tumor cell is a thyroid cancer cell.

16. The method according to claim 8, wherein said tumor cell is an ovarian cancer cell.

17. The method according to claim 8, wherein said tumor cell is a prostate cancer cell.

18. A method of treating cancer comprising administering to a subject having a cancer an effective amount of a composition comprising an siRNA molecule or an antisense oligonucleotide that inhibits the activity of protein kinase N beta by causing degradation of a ribonucleic acid encoding protein kinase N beta, wherein protein kinase N beta is up-regulated in the cells of said cancer as compared to non-cancer cells of the same lineage.

19. The method according to claim 18, wherein said composition comprises an antisense oligonucleotide.

20. The method according to claim 18, wherein said composition comprises an siRNA molecule.

21. The method according to claim 18, wherein said cancer cell is an endometrial cancer cell; a colorectal carcinoma cell; a glioma cell; an adenocarcinoma cell; a breast cancer cell; a thyroid cancer cell; an ovarian cancer cell; or a prostate cancer cell.

22. The method according to claim 21, wherein said cancer cell is an endometrial cancer cell.

23. The method according to claim 21, wherein said tumor cell is a colorectal carcinoma cell.

24. The method according to claim 21, wherein said tumor cell is a glioma cell.

25. The method according to claim 21, wherein said tumor cell is an adenocarcinoma cell.

26. The method according to claim 21, wherein said tumor cell is a breast cancer cell.

27. The method according to claim 21, wherein said tumor cell is a thyroid cancer cell.

28. The method according to claim 21, wherein said tumor cell is an ovarian cancer cell.

29. The method according to claim 21, wherein said tumor cell is a prostate cancer cell.

30. The method according to claim 1, wherein said ribonucleic acid encodes SEQ ID NO: 1.

31. The method according to claim 5, wherein said ribonucleic acid encodes SEQ ID NO: 1.

32. The method according to claim 18, wherein said ribonucleic acid encodes SEQ ID NO: 1.

* * * * *

UNITED STATES PATENT AND TRADEMARK OFFICE
CERTIFICATE OF CORRECTION

PATENT NO. : 7,713,943 B2 Page 1 of 3
APPLICATION NO. : 10/640274
DATED : May 11, 2010
INVENTOR(S) : Anke Klippel-Giese et al.

It is certified that error appears in the above-identified patent and that said Letters Patent is hereby corrected as shown below:

Column 3,
Line 35, "MRNA" should read --mRNA--.

Column 4,
Line 36, "stenth" should read --tenth--.
Line 58, "wherein" should read --wherein:--.

Column 5,
Line 49, "volume-of" should read --volume of--.

Column 6,
Line 19, "with he" should read --with the--.

Column 7,
Line 61, "pateinets with liver metasasis" should read --patients with liver metastasis--.

Column 10,
Line 22, "MnRNA" should read --mRNA--.
Line 51, "related to to" should read --related to--.

Column 11,
Line 14, "nead neck" should read --head, neck--.
Lines 14-15, "leiomyosarcoma metastatic" should read --leiomyosarcoma, metastatic--.

Column 12,
Line 44, "MRNA" should read --mRNA--.

Column 13,
Line 34, "MRNA" should read --mRNA--.

Signed and Sealed this

Twelfth Day of October, 2010

David J. Kappos
*Director of the United States Patent and Trademark Office*

Column 15,
Line 3, "certain extend" should read --certain extent--.
Line 16, "having a lengths" should read --having lengths--.
Line 67, "Examples if" should read --Examples of--.

Column 16,
Line 35, "stabilized -such" should read --stabilized such--.

Column 17,
Line 40, "MRNA" should read --mRNA--.

Column 18,
Line 2, "20017: 221-8)." should read --2001 7: 221-8).--.

Column 20,
Line 4, "2'-O-methylribonucleotides S is connected" should read
    --2'-O-methylribonucleotides is connected--.
Line 16, "cap-nnnnnnnNNNNNNNNnnnnnnnn-cap" should read
    --cap-nnnnnnnNNNNNNNNNnnnnnnnn-cap--.
Lines 29-31, "cap-$(n_p)_5(N_s)_9(n_p)$s-cap, cap-$(n_p)_6$(NS)$_9(n_p)$S-cap, cap-$(n_p)7$(NS)g$(n_p)_5$-cap,
    cap-$(n_p)_5$(NS)$_7(n_p)_6$-cap" should read --cap-$(n_p)_5(N_s)_9(n_p)_5$-cap,
    cap-$(n_p)_6(N_s)_9(n_p)_5$-cap, cap-$(n_p)_7(N_s)_9(n_p)_5$-cap, cap-$(n_p)_5(N_s)_7(n_p)_6$-cap--.
Line 35, "cap-$(n_p)_7(N_s)_7(n_p)_7$cap" should read --cap-$(n_p)_7(N_s)_7(n_p)_7$-cap--.
Lines 35-36, "cap-$(n_p)_5$(NS)s$(n_p)_7$-cap" should read --cap-$(n_p)_5(N_s)_8(n_p)_7$-cap--.
Lines 36-37, "cap-$(n_p)_7(N_s)$g$(n_p)_7$-cap" should read --cap-$(n_p)_7(N_s)_8(n_p)_7$-cap--.
Line 38, "cap-$(n_p)_7$(NS)$_9(n_p)_7$-cap" should read --cap-$(n_p)_7(N_s)_9(n_p)_7$-cap--.
Line 45, "MRNA" should read --mRNA--.
Line 52, "MRNA" should read --mRNA--.
Line 54, "MRNA" should read --mRNA--.
Line 56, "MRNA" should read --mRNA--.

Column 22,
Line 41, "Oligofectarnine" should read --Oligofectamine--.
Line 64, "Fam-Tainra" should read --Fam-Tamra--.
Line 65, "in 50gl" should read --in 50 μl--.

Column 23,
Line 6, "trnasfected" should read --transfected--.
Line 67, "glas" should read --glass--.

Column 24,
Line 48, "Smg" should read --5mg--.

Column 25,
Line 44, "determined" should read --determined.--.
Line 55, "confirmned" should read --confirmed--.

Column 26,
Line 1, "Stemberger" should read --Sternberger--.
Lines 33-34, "linkage" should read --linkage.--.

Column 27,
Line 16, "siRNA" should read --mRNA--.

Column 28,
Line 60, "MRNA" should read --mRNA--.

Column 29,
Line 34, "b) αN" should read --b) ΔN--.

Column 30,
Line 39, "AN" should read --ΔN--.

Column 32,
Line 26, "proteinss," should read --proteins,--.
Lines 44-45, "anti-phopho-GSK3" should read --anti-phospho-GSK3--.

Column 34,
Line 35, "perneabilization" should read --permeabilization--.